United States Patent
Hong et al.

(10) Patent No.: US 8,222,040 B2
(45) Date of Patent: Jul. 17, 2012

(54) NUCLEIC ACID SEQUENCING BY SELECTIVE EXCITATION OF MICROPARTICLES

(75) Inventors: Stanley S. Hong, Palo Alto, CA (US); Jekwan Ryu, Cupertino, CA (US); Jong Buhm Park, Sunnyvale, CA (US)

(73) Assignee: LightSpeed Genomics, Inc., Santa Clara, CA (US)

( * ) Notice: Subject to any disclaimer, the term of this patent is extended or adjusted under 35 U.S.C. 154(b) by 934 days.

(21) Appl. No.: 11/846,049

(22) Filed: Aug. 28, 2007

(65) Prior Publication Data

US 2009/0061526 A1 Mar. 5, 2009

(51) Int. Cl.
*G01N 21/63* (2006.01)
*G06K 9/00* (2006.01)
*C12Q 1/68* (2006.01)

(52) U.S. Cl. ............ 436/94; 436/164; 382/129; 702/20; 435/6.1; 435/287.2

(58) Field of Classification Search ................. None
See application file for complete search history.

(56) References Cited

U.S. PATENT DOCUMENTS

| | | |
|---|---|---|
| 3,780,217 A | 12/1973 | Sawatari |
| 5,041,733 A | 8/1991 | Noguchi et al. |
| 5,470,710 A | 11/1995 | Weiss et al. |
| 5,674,698 A | 10/1997 | Zarling et al. |
| 5,695,934 A | 12/1997 | Brenner |
| 5,750,341 A | 5/1998 | Macevicz |
| 5,751,243 A | 5/1998 | Turpin |
| 5,763,175 A | 6/1998 | Brenner |
| 5,780,231 A | 7/1998 | Brenner |
| 5,902,723 A * | 5/1999 | Dower et al. ............... 435/6 |
| 5,969,119 A | 10/1999 | Macevicz |
| 6,013,445 A | 1/2000 | Albrecht et al. |
| 6,016,196 A | 1/2000 | Mermelstein |
| 6,140,660 A | 10/2000 | Mermelstein |
| 6,306,597 B1 | 10/2001 | Macevicz |

(Continued)

FOREIGN PATENT DOCUMENTS

KR 10-2000-0004675 1/2000

(Continued)

OTHER PUBLICATIONS

Ryu, "Resolution Improvement in Optical Microscopy by Use of Multi-Beam Interferometric Illumination," Ph.D. Dissertation, Massachusetts Institute of Technology, 2003.*

(Continued)

*Primary Examiner* — Yelena G Gakh
*Assistant Examiner* — Michelle Adams
(74) *Attorney, Agent, or Firm* — Fenwick & West LLP

(57) ABSTRACT

Nucleic acid microparticles are sequenced by performing a sequencing reaction on the microparticles using one or more reagents, selectively exciting the microparticles in an excitation pattern, optically imaging the microparticles at a resolution insufficient to resolve individual microparticles, and processing the optical images of the microparticles using information on the excitation pattern to determine the presence or absence of the optical signature, which indicates the sequence information of the nucleic acid. An apparatus for optical excitation of the microparticles comprises an optical fiber delivering a first laser beam, and an interference pattern generation module coupled to the optical fiber. The interference pattern generation module splits the first laser beam into second and third laser beams and generates the excitation pattern for selectively exciting the microparticles by interference between the second and third laser beams.

16 Claims, 20 Drawing Sheets

U.S. PATENT DOCUMENTS

| | | | |
|---|---|---|---|
| 6,406,848 | B1 | 6/2002 | Bridgham et al. |
| 6,525,875 | B1 | 2/2003 | Lauer |
| 6,548,820 | B1 | 4/2003 | Mermelstein |
| 6,654,505 | B2 | 11/2003 | Bridgham et al. |
| 6,787,308 | B2 | 9/2004 | Balasubramanian et al. |
| 6,806,052 | B2 | 10/2004 | Bridgham et al. |
| 6,831,994 | B2 | 12/2004 | Bridgham et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,122,384 | B2 | 10/2006 | Prober et al. |
| 7,169,560 | B2 | 1/2007 | Lapidus et al. |
| 7,211,390 | B2 | 5/2007 | Rothberg et al. |
| 7,248,338 | B2 | 7/2007 | Fukuda |
| 7,397,018 | B1 | 7/2008 | Pham et al. |
| 7,405,114 | B2 | 7/2008 | Oishi |
| 7,602,501 | B2 | 10/2009 | Ralston et al. |
| 7,639,909 | B2 | 12/2009 | Murshid et al. |
| 7,916,144 | B2 | 3/2011 | Schiwietz et al. |
| 2001/0029785 | A1* | 10/2001 | Heaslip et al. ............... 73/579 |
| 2002/0051992 | A1 | 5/2002 | Bridgham et al. |
| 2002/0061529 | A1 | 5/2002 | Bridgham et al. |
| 2002/0137052 | A1 | 9/2002 | Bridgham et al. |
| 2003/0077615 | A1 | 4/2003 | Bridgham et al. |
| 2003/0224419 | A1 | 12/2003 | Corcoran et al. |
| 2005/0099682 | A1 | 5/2005 | Lauer |
| 2005/0100932 | A1 | 5/2005 | Lapidus et al. |
| 2005/0221351 | A1 | 10/2005 | Ryu |
| 2005/0239113 | A1 | 10/2005 | Ryu et al. |
| 2005/0239114 | A1 | 10/2005 | Ryu et al. |
| 2005/0239115 | A1 | 10/2005 | Ryu et al. |
| 2005/0286576 | A1 | 12/2005 | Gill et al. |
| 2006/0012784 | A1 | 1/2006 | Ulmer |
| 2006/0012793 | A1 | 1/2006 | Harris |
| 2006/0024711 | A1 | 2/2006 | Lapidus et al. |
| 2006/0051876 | A1 | 3/2006 | Bridgham et al. |
| 2006/0146334 | A1 | 7/2006 | Cluff et al. |
| 2006/0263777 | A1 | 11/2006 | Tong |
| 2006/0274408 | A1 | 12/2006 | Lauer |
| 2007/0031875 | A1 | 2/2007 | Buzby |
| 2007/0070349 | A1 | 3/2007 | Harris et al. |
| 2007/0087362 | A1 | 4/2007 | Church et al. |
| 2007/0099208 | A1 | 5/2007 | Drmanac et al. |

FOREIGN PATENT DOCUMENTS

| | | |
|---|---|---|
| WO | WO 2009/032510 | 3/2009 |

OTHER PUBLICATIONS

Cragg, et al. "Lateral resolution enhancement with standing evanescent waves," Opt. Lett. 2000, 25, 46-48.*

PCT International Search Report and Written Opinion, PCT Application No. PCT/US08/73353, Nov. 10, 2008, 8 pages.

PCT International Search Report and Written Opinion, PCT Application No. PCT/US08/73349, Nov. 19, 2008, 11 pages.

Freimann, R., et al., "Development of a standing-wave fluorescence microscope with high nodal plane flatness," Journal of Microscopy, Sep. 1997, pp. 193-200, vol. 187, Pt. 3.

Frohn, J., et al., "True optical resolution beyond the Rayleigh limit achieved by standing wave illumination," PNAS, Jun. 20, 2000, pp. 7232-7236, vol. 97, No. 13.

Frohn, J., et al., "Three-dimensional resolution enhancement in fluorescence microscopy by harmonic excitation," Optic Letters, Jun. 1, 2001, pp. 828-830, vol. 26, No. 11.

Gustafsson, M.G.L., "Surpassing the lateral resolution limit by a factor of two using structured illumination microscopy," Journal of Microscopy, May 2000, pp. 82-87, vol. 198, Pt. 2.

Hong, S., et al., "Lensless focusing with subwavelength resolution by direct synthesis of the angular spectrum," Applied Physics Letters, Jun. 29, 2006, vol. 88, pp. 261107-1-261107-3.

Kim, J., et al. "Polony Multiplex Analysis of Gene Expression (PMAGE) in Mouse Hypertrophic Cardiomyopathy," Science, Jun. 8, 2007, pp. 1481-1484, vol. 316, with Supporting Online Material downloaded from the Internet at http://www.sciencemag.org/cgi/data/316/5830/1481/DC1/2 attached.

Ryu, J., et al., "Multibeam interferometric illumination as the primary source of resolution in optical microscopy," Applied Physics Letters, Apr. 28, 2006, vol. 88, pp. 171112-1-171112-3.

Shendure, J., et al., "Accurate Multiplex Polony Sequencing of an Evolved Bacterial Genome," Science, Sep. 9, 2005, pp. 1728-1732, vol. 309, with Supporting Online Material downloaded from the Internet at http://www.sciencemag.org/cgi/data/1117389/DC1/1 attached.

Ryu, J., "Resolution Improvement in Optical Microscopy by Use of Multi-Beam Interferometric Illumination," Ph.D. Dissertation, Massachusetts Institute of Technology, Sep. 2003, 122 pages.

Chinese State Intellectual Property Office, First Office Action, Chinese Application No. 200880104704.6, Dec. 19, 2011, seventeen pages.

Chinese State Intellectual Property Office, First Office Action, Chinese Application No. 200880104651.8, Mar. 20, 2012, fifteen pages.

Korean Intellectual Property Office, Office Action, Korean Patent Application No. 10-2010-7004823, Mar. 22, five pages.

PCT International Search Report and Written Opinion, PCT Application No. PCT/US2011/028792, May 26, 2011, seven pages.

PCT International Search Report and Written Opinion, PCT Application No. PCT/US2011/028796, May 13, 2011, eight pages.

Korean Intellectual Property Office, Office Action, Korean Patent Application No. 10-2010-7004823, Aug. 30, 2011, seven pages.

Korean Intellectual Property Office, Office Action, Korean Patent Application No. 10-2010-7004824, Oct. 21, 2011, eleven pages.

Zhi, Z. et al., "Microfabrication of Encoded Microparticle Array for Multiplexed DNA Hybridization Detection," *Chem. Commun.*, 2005, pp. 2448-2450.

* cited by examiner

NUCLEIC ACID SEQUENCING BY SELECTIVE EXCITATION OF MICROPARTICLES

CROSS-REFERENCE TO RELATED APPLICATION

This application is related to U.S. patent application Ser. No. 11/846,067, entitled "Apparatus for Selective Excitation of Microparticles," filed on Aug. 28, 2007.

BACKGROUND OF THE INVENTION

1. Field of the Invention

The present invention relates generally to the field of nucleic acid sequencing and, more specifically, to a method and system for DNA (deoxyribonucleic acid) sequencing by selective excitation of microparticles.

2. Description of the Related Art

FIG. 1 illustrates a conventional method of DNA sequencing with microparticles. The method of FIG. 1 derives DNA sequence data 112 from a microparticle array 102 through cycles of sequencing reactions 104, non-selective excitation 106 of the microparticles, and optical signature detection 108. Each microparticle in the microparticle array 102 typically contains DNA molecules with both unknown sequences to be determined and known sequences that are used in the sequencing reactions. Thousands to millions (to potentially billions or more) of these microparticles are distributed and immobilized on the surface of a glass substrate, as conceptually shown in FIG. 2, which illustrates an example of a microparticle array 102. The microparticle array 102 includes DNA sequencing microparticles 204 distributed and immobilized on a substrate 202. The microparticles 204 can take many forms, such as 1-micron diameter beads covered with DNA molecules amplified by a water-in-oil emulsion PCR (polymerase chain reaction) technique, or clusters of DNA molecules amplified by a bridge amplification technique, or individual unamplified DNA molecules. The microparticles 204 can be distributed either randomly (e.g., irregularly spaced) or in an orderly pattern (e.g., regularly spaced pattern such as a square grid pattern or a hexagonal grid pattern) on the substrate 202. The substrate 202 is typically made of glass and located inside a flow cell, which allows the microparticles 204 to be exposed to a series of reagents to perform sequencing reactions. At the end of each cycle of sequencing reactions, each microparticle takes on an optical signature, often as the result of the incorporation of one of the four fluorophores such as Cy3, Cy5, Texas Red, and a fluorescence resonance energy transfer (FRET) pair, that reveals the corresponding bases adenine (abbreviated "a"), cytosine (abbreviated "c"), guanine (abbreviated "g") and thymine (abbreviated "t") of the DNA.

FIGS. 3A-3C illustrate different types of individual sequencing microparticles that can be used for DNA sequencing. FIG. 3A illustrates an individual microparticle 204 formed by a 1-micrometer diameter bead 302 covered with clonal DNA molecules 304 that have been previously amplified by a water-in-oil emulsion PCR technique. The bead 302 is attached directly to the substrate 202 in fluid 306. FIG. 3B illustrates an individual microparticle 204 as a cluster of clonal DNA molecules 304 attached to the substrate 202 and placed in fluid 306. The DNA molecules have been previously amplified by a bridge amplification technique. FIG. 3C illustrates an individual microparticle as a single DNA molecule 304 attached to the substrate 202 and placed in fluid 306. The single DNA molecule 304 is sequenced without amplification.

Referring back to FIG. 1 together with FIGS. 2 and 3A-3C, DNA sequencing with microparticles includes performing a sequencing reaction 104 on the microparticle array 102 to cause each microparticle 204 to take on an optical signature that reveals the DNA sequence information. The microparticle array 102 is exposed to sequencing reagents, which enables each cycle of sequencing reactions to be performed in a massively parallel manner. For example, one cycle of sequencing reaction can be comprised of hybridizing anchor primers and ligating a pool of fluorescently-labeled query primers. At the end of each cycle of sequencing reactions 104, each microparticle takes on an optical signature that reveals the DNA sequence information associated with that microparticle. For example, the optical signature can be the result of the incorporation of one of four fluorophores corresponding to bases "a," "c," "g," and "t" of the DNA 304.

The next step is to optically excite 106 the microparticles 204 and to detect 108 the optical signatures of the microparticles. As will be explained with reference to FIGS. 4A-4C, the conventional optical excitation is non-selective. This cycle of reaction 104, non-selective excitation 106, and optical signature detection 108 is repeated multiples times to sequence the DNA 304 in each microparticle 204. DNA sequence data 112 is output from this process.

Conventional DNA sequencing methods with microparticles suffer from low throughput (measured in bases per second) because the rate at which the optical signatures of the microparticles are detected is limited. This is largely due to the use of conventional non-selective excitation patterns, followed by optical imaging using optical microscopy, as used in conventional DNA sequencing methods. FIGS. 4A-4C illustrate conventional non-selective excitation patterns used to excite the microparticles for subsequent imaging using optical microscopy. Specifically, FIG. 4A illustrates a wide-field excitation pattern 402 used with the microparticles 204 on the substrate 202, where all the microparticles in the field of view (FOV) are illuminated. FIG. 4B illustrates line-scanning excitation, where the microparticles 204 are illuminated by a line of light 402 that scans the substrate 202. FIG. 4C illustrates spot-scanning excitation, where the microparticles 204 are illuminated by a spot of light 406 that scans the substrate 202.

Conventional non-selective excitation patterns can be generated by a variety of means. A wide-field excitation pattern 402 is typically generated by focusing an arc lamp source through the microscope optical train in a Kohler epi-illumination configuration, or by shining a laser source at a steep angle in an off-axis or total internal reflection (TIR) illumination configuration. A line-scanning excitation pattern 404 is typically generated by focusing a spatially-coherent laser through the microscope optical train and incorporating a scanning element. A spot-scanning excitation pattern 406 is typically generated by focusing a spatially-coherent laser source through the microscope optical train in a confocal configuration.

In such conventional DNA sequencing methods, detection of the microparticle optical signatures is typically performed by optical-microscope imaging of the microparticles illuminated with non-selective excitation patterns as shown in FIGS. 4A-4C. The speed of this approach is limited fundamentally for several reasons. First, the field of view (FOV) of an optical microscope is coupled fundamentally to resolution, i.e., the higher the resolution, the smaller the FOV. Similarly, the depth of field (DOF) of an optical microscope is coupled fundamentally to resolution, i.e., the higher the resolution, the smaller the DOF. Because a high-resolution optical microscope is required to resolve the microparticles using conventional sequencing methods, the FOV and DOF are relatively small. Consequently, imaging a microparticle substrate requires the acquisition of hundreds to thousands of smaller images that collectively cover the slide like tiles. Between each image, either the substrate or the optical microscope must be translated and focused precisely with respect to the microscope objective, during which time the optical microscope cannot be acquiring sequence data. Second, a high-resolution image of a microparticle slide is a very inefficient representation of the sequence information contained in the microparticles. For example, in a typical high-resolution image of a microparticle slide, the number of pixels in the image greatly exceeds the number of microparticles in the image. However, assuming that each microparticle can take on one of only four optical signatures, each microparticle carries just 2 bits of sequence information. Consequently, several thousands times more data is acquired than is necessary to generate the sequence information, according to conventional sequencing methods.

Thus, there is a need for a more efficient, faster, and more convenient method of nucleic acid sequencing.

SUMMARY OF THE INVENTION

Embodiments of the present invention include a method of sequencing nucleic acids such as DNA or RNA (ribonucleic acid) with fast speed by selectively exciting the nucleic acid microparticles and using image processing algorithms to extract the optical signatures of the microparticles. The term "nucleic acid" herein includes both DNA and RNA. An advantage of this approach is that it allows a relatively low-resolution optical microscope to image the selectively-excited microparticles, which enables detection of microparticle optical signatures to be performed with an extremely large field of view (FOV) and depth of field (DOF). Another advantage of this approach is that relatively low-resolution images of microparticles with selective excitation are a more efficient data representation of the sequence information than high-resolution images of microparticles with non-selective excitation, which enables the amount of acquired data required for sequencing to be greatly reduced.

In one embodiment, a method for sequencing nucleic acid microparticles comprises performing a sequencing reaction on the nucleic acid microparticles using one or more sequencing reagents, selectively exciting the nucleic acid microparticles in an excitation pattern, optically imaging the excited nucleic acid microparticles at a resolution insufficient to resolve individual microparticles, and processing the optical images of the excited nucleic acid microparticles using information on the excitation pattern to determine the presence or absence of at least an optical signature. The presence or absence of the optical signature indicates sequence information of the nucleic acid. Although the images of the excited nucleic acid microparticles are obtained at a resolution insufficient to resolve individual microparticles, the selective excitation of the nucleic acid microparticles is performed at a resolution sufficient to resolve the individual microparticles. The sequencing reaction, selective excitation, and image processing steps can be repeated using same or different reagents to complete the sequencing.

In one embodiment, an apparatus for optical excitation of the nucleic acid microparticles comprises a laser for generating a first laser beam, an optical fiber coupled to receive the first laser beam, an interference pattern generation module coupled to the first optical fiber and for receiving the first laser beam delivered via the optical fiber, where the interference pattern generation module splits the first laser beam into a second laser beam and a third laser beam and generates the excitation pattern for selectively exciting the target by interference between the second laser beam and the third laser beam.

The interference pattern generation module can include a beam splitter for splitting the first laser beam into the second laser beam and the third laser beam, and a mirror reflecting the third laser beam where the mirror is movable within a range to vary an optical path-length of the third laser beam. Alternatively, the interference pattern generation module can include a beam splitter for splitting the first laser beam into the second laser beam and the third laser beam, and a window coupled to the third laser beam and rotating to modulate the optical phase of the third laser beam.

The nucleic acid sequencing method of the present invention is fast and efficient for at least two reasons. First, since the FOV and DOF for detection of microparticle optical signatures are increased, the mechanical motion required for scanning and focusing is greatly reduced. Second, since the amount of acquired data required for sequencing is reduced (by use of low-resolution images insufficient to resolve individual microparticles enabled by use of the information on the excitation pattern in processing the optical images), the time required for sequencing is greatly reduced.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The teachings of the embodiments of the present invention can be readily understood by considering the following detailed description in conjunction with the accompanying drawings.

DETAILED DESCRIPTION OF EMBODIMENTS

The Figures (FIG.) and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments of the present invention(s), examples of which are illustrated in the accompanying figures. It is noted that wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

Figure 5:
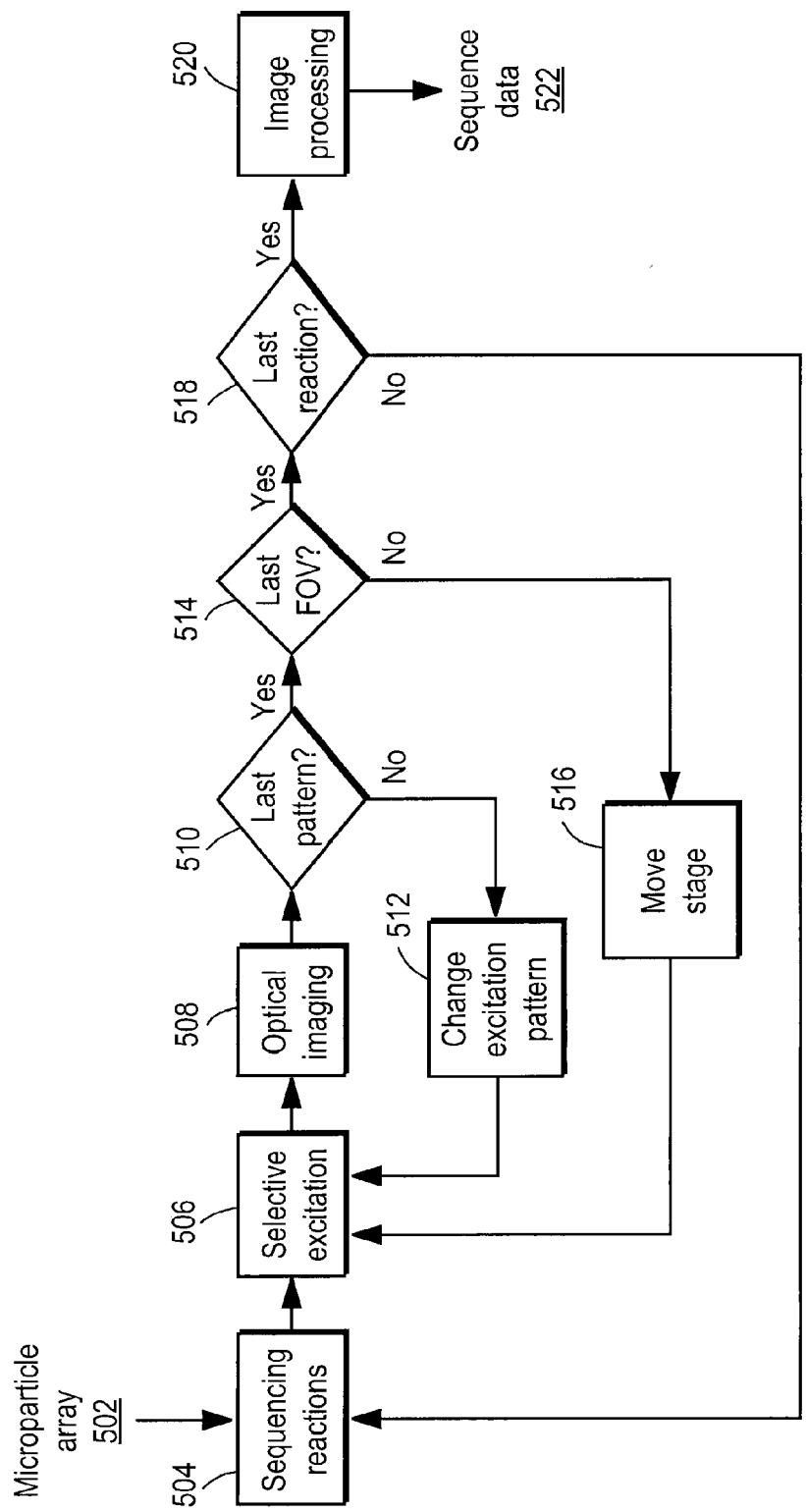
FIG. 5 illustrates a method of nucleic acid (e.g., DNA or RNA) sequencing by selective excitation of microparticles using structured illumination, according to one embodiment of the present invention.

FIG. 5 illustrates a method of nucleic acid (e.g., DNA or RNA) sequencing by selective excitation of microparticles using structured illumination. Although the disclosure herein describes the nucleic acid sequencing method in the context of DNA sequencing, the use of the term "sequencing" is not intended to limit the scope of the present invention to DNA sequencing, and "sequencing" herein does include RNA sequencing or other types of nucleic acid sequencing. "Sequencing" or "sequence" herein is also intended to cover all sequence variations, such as single nucleotide polymorphisms (SNPs), gene copy number variations, single base duplications, inversions, insertions and deletions and all the applications of such sequencing, such as genotyping, gene expression analysis, and medical applications.

Figure 1:
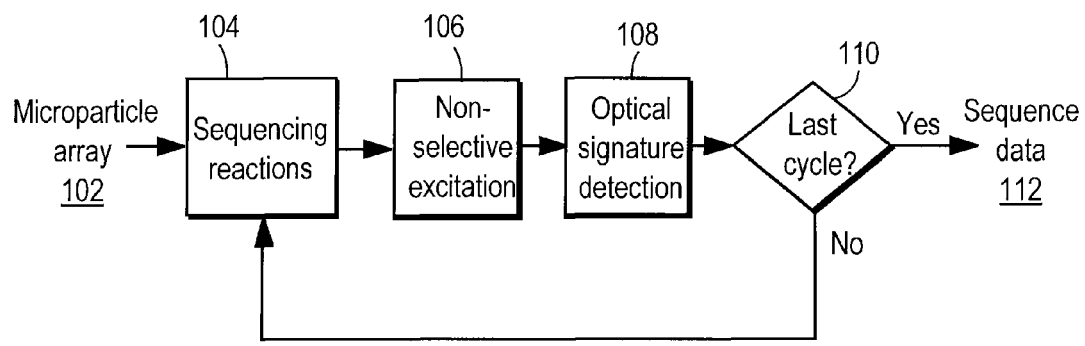
FIG. 1 illustrates a conventional method of DNA sequencing with microparticles.
Figure 2:
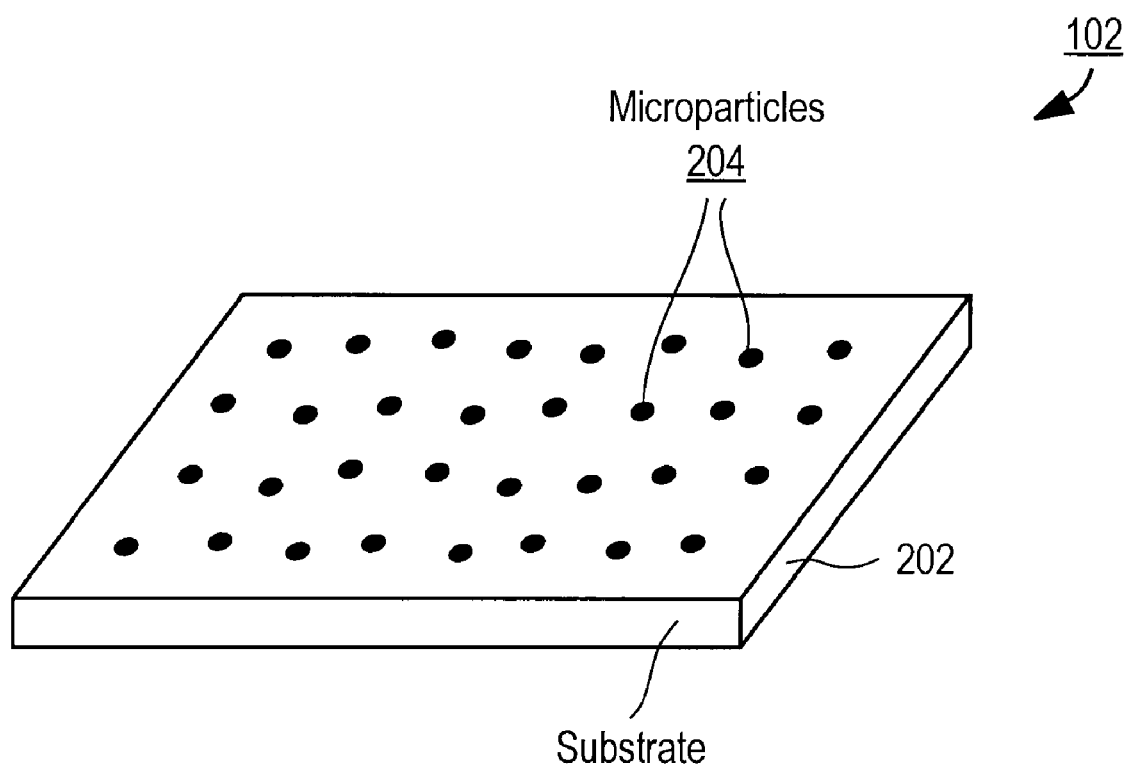
FIG. 2 illustrates an example of a microparticle array.
Figure 3A:
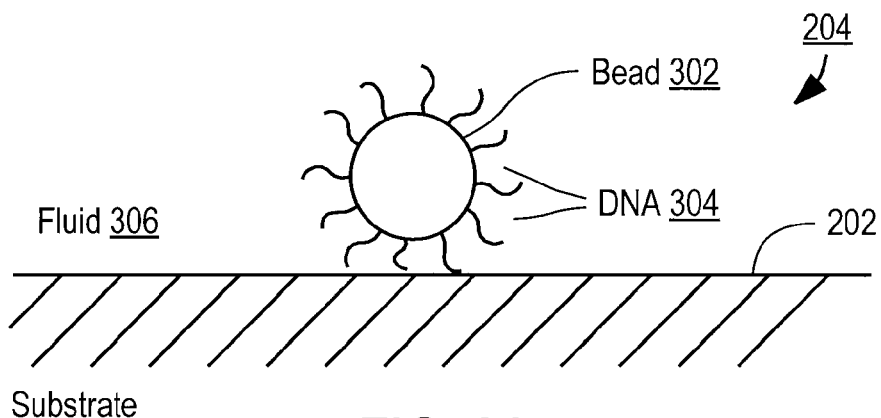
FIGS. 3A, 3B, and 3C illustrate different types of individual sequencing microparticles that can be used for DNA sequencing.
Figure 3B:
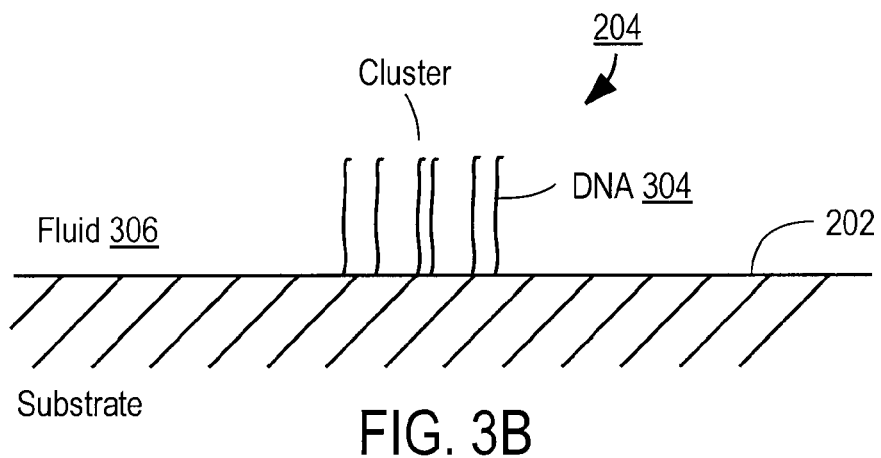
Figure 3C:
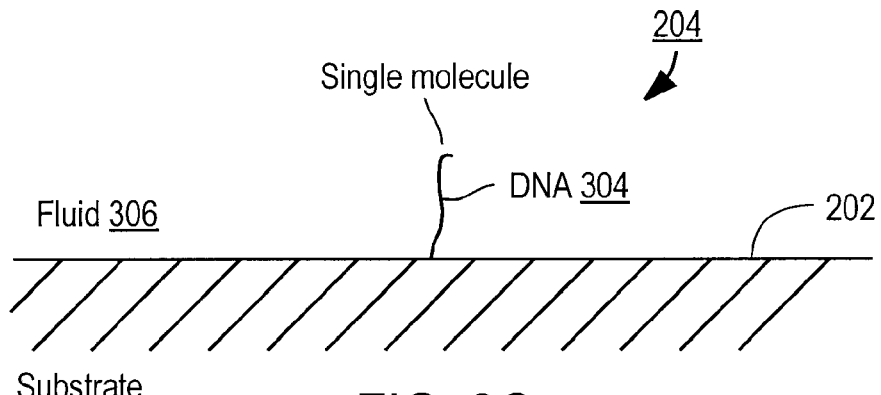

The microparticle array 502 with the DNA first undergoes a cycle of sequencing reactions 504. The sequencing reactions 504 include exposing the microparticles to a series of reagents and incubating the microparticles at a series of temperatures. As the end-product of the sequencing reaction cycle, each microparticle takes on an optical signature that reveals the sequence information associated with that microparticle. The optical signature can be the result of the incorporation of one or more optically detectable labels, such as fluorescent dyes, colloidal gold, and quantum dots. For example, each sequencing reaction 504 can be designed such that the optical signature is the result of the incorporation of one of four fluorophores corresponding to the bases "a," "c," "g," and "t" of the DNA 304. Note that the microparticles can be one of the types shown in FIGS. 3A-3C or some other type suitable for DNA sequencing. Also note that a number of additional conventional steps may have to be performed to prepare the microparticle array with the DNA from the DNA sample, which are not the subject of the present invention and are not described herein.

In contrast to conventional DNA sequencing methods, the microparticles 204 are then selectively excited 506 with a selective excitation pattern, as is explained in more detail with reference to FIGS. 6A-6C. The selectively-excited microparticle array is then imaged 508 using an optical microscope. Then, it is determined 510 whether the current selective excitation pattern is the last pattern to apply. If it is not the last pattern, the excitation pattern is then changed 512, and the excite-and-image cycle in steps 506, 508, 510 is repeated.

Figure 6A:
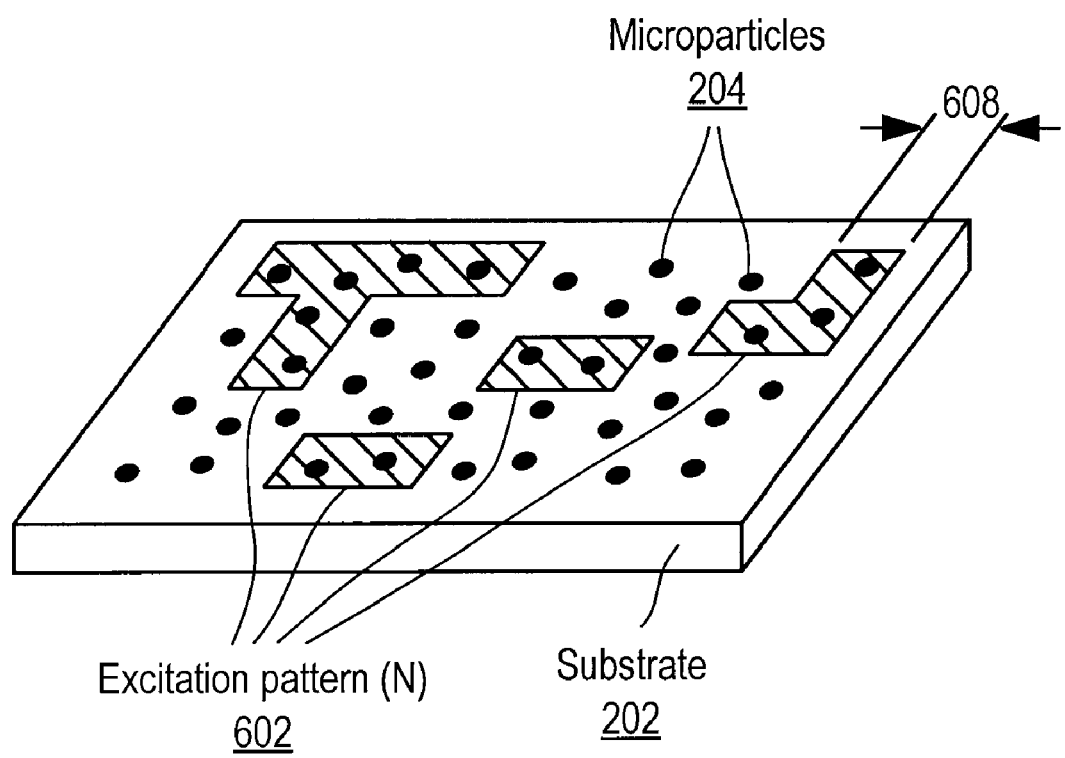
FIGS. 6A, 6B, and 6C illustrate how the microparticles are selectively excited by a sequence of excitation patterns, according to one embodiment of the present invention.
Figure 6B:
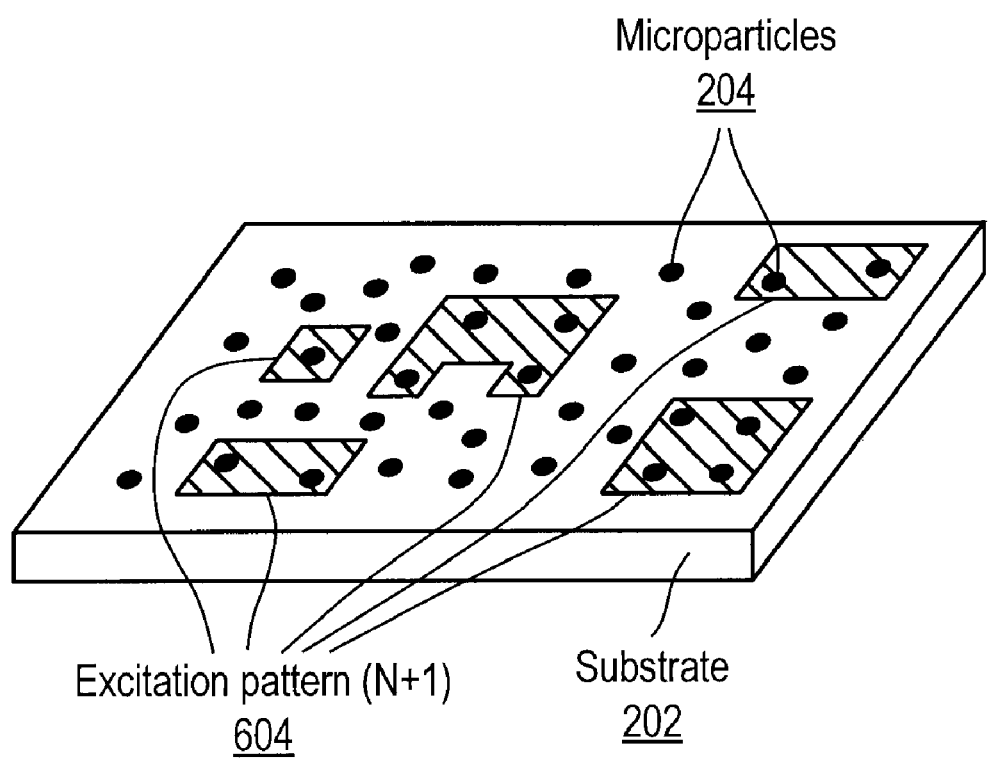
Figure 6C:
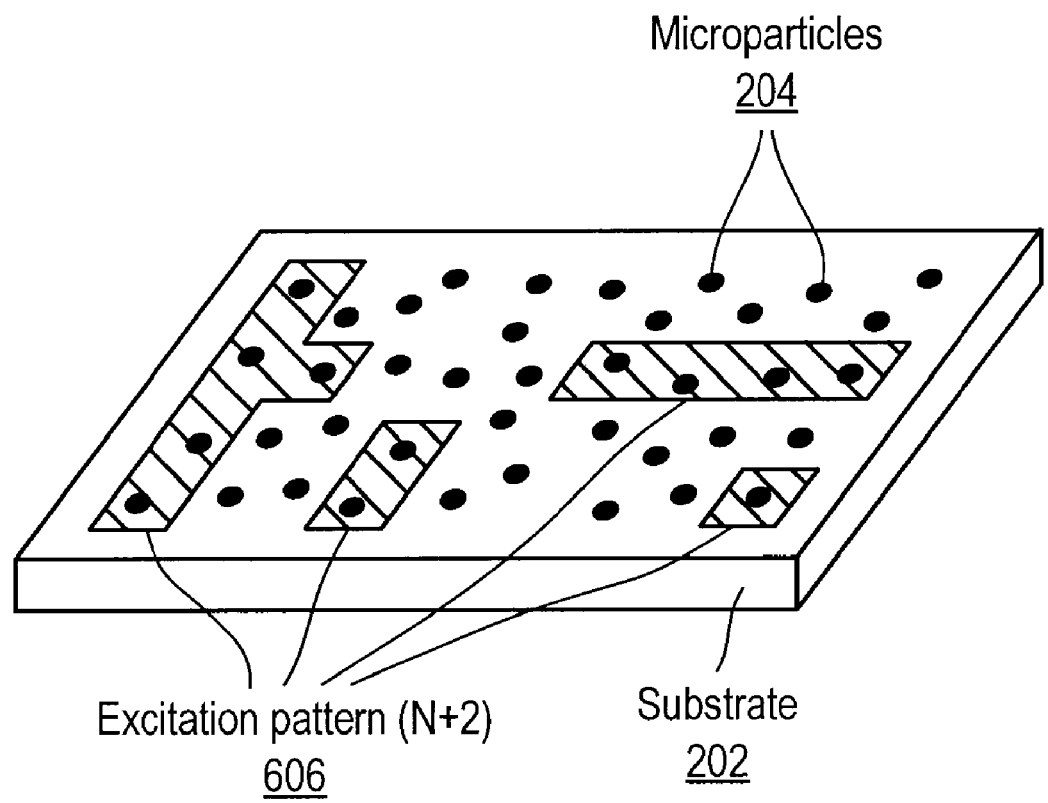

FIGS. 6A-6C illustrate how the microparticles are selectively excited by a sequence of excitation patterns as shown in the excite-and-image cycle in steps 506, 508, 510. Referring to FIG. 6A, a selective excitation pattern 602 is generated on the microparticles 204 at time N. Referring to FIG. 6B, another selective excitation pattern 604 is generated on the microparticles 204 at time N+1. Referring to FIG. 6C, still another selective excitation pattern 606 is generated on the microparticles 204 at time N+2.

Figure 4A:
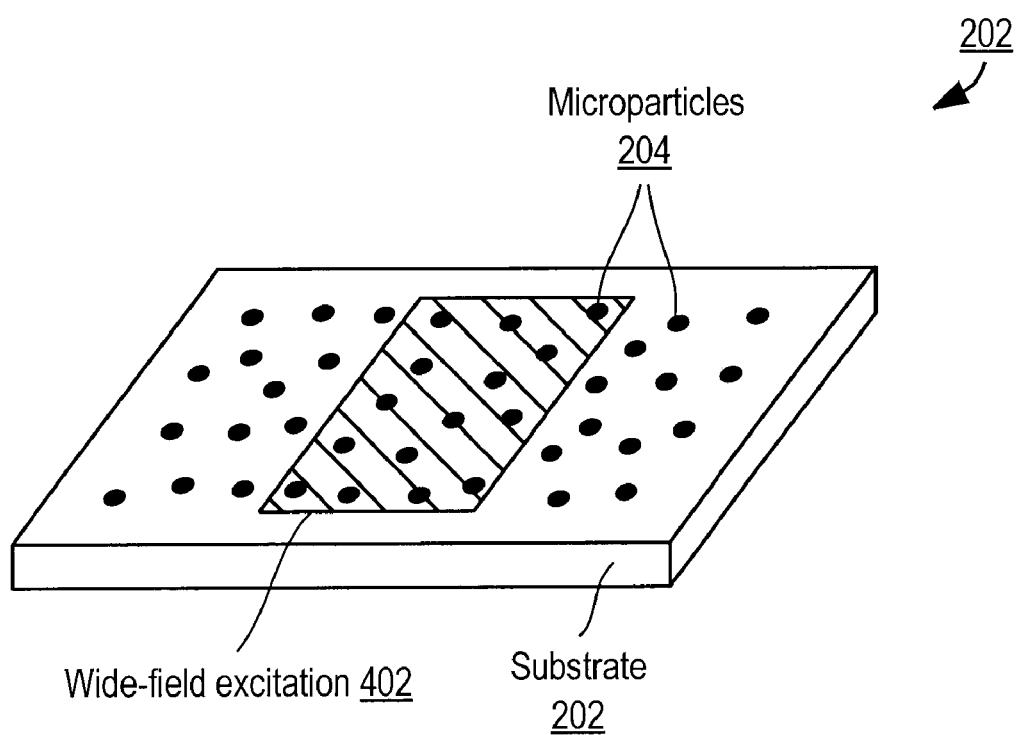
FIGS. 4A, 4B, and 4C illustrate conventional non-selective excitation patterns used to excite the microparticles.
Figure 4B:
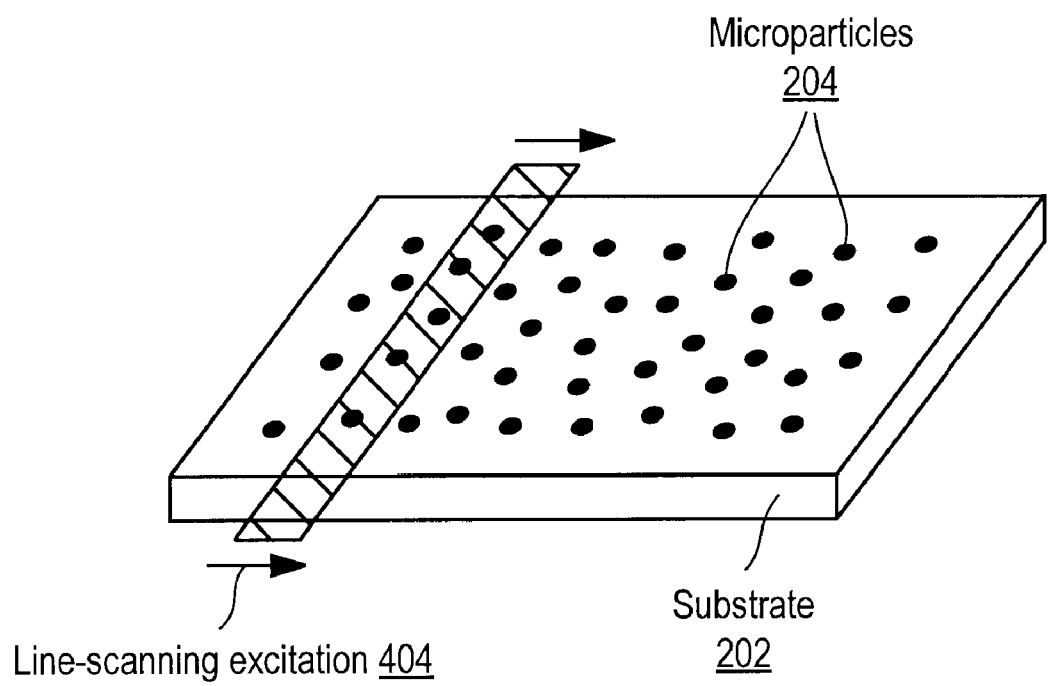
Figure 4C:
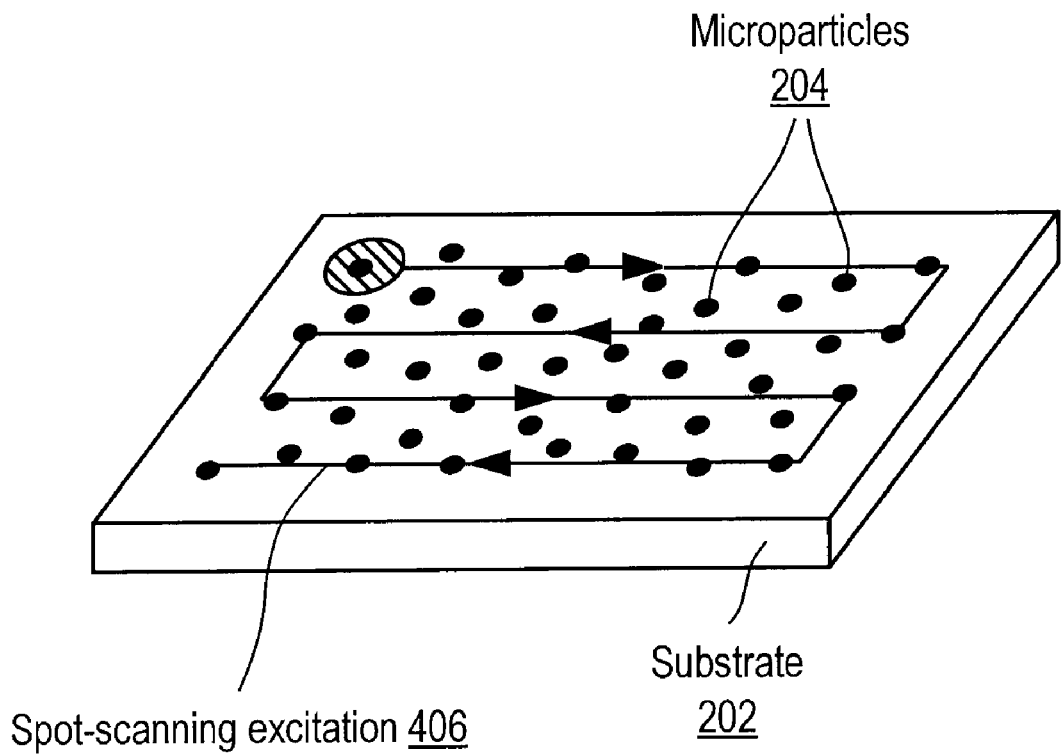

Note that these selective excitation patterns 602, 604, 606 are "selective" in that they excite the microparticles 204 in a non-trivial sequence of patterns. In contrast, the conventional excitation patterns shown in FIGS. 4A-4C indiscriminately excite a region of space in a trivial pattern with the goal of producing an image (i.e., a photographic replica) of the region as a function of space and/or time. For example, the widefield scanning excitation of FIG. 4A produces an image of the region as a function of space in two dimensions. The linescanning excitation of FIG. 4B produces an image of the region as a function of space in one dimension and time in one dimension. The spot-scanning excitation of FIG. 4C produces an image of the region as a function of time in two dimensions. In other words, conventional excitation is used to generate a single high-resolution image that is a photographic replica of the microparticle array 502. In contrast, selective excitation according to the present invention is used to generate a sequence of low-resolution images of the microparticle array 502 in which the low-resolution images are not photographic replicas of the microparticle array 502; instead, selective excitation encodes the sequence information in the set of low-resolution images (with the resolution not being high enough to resolve the individual microparticles 204), and the images are processed using knowledge of the selective excitation patterns to decode the sequence information. Also, the use of conventional excitation entails little more than simply translating a trivial excitation pattern, such as a rectangle 402, a line 404, or a circle 406. In contrast, the use of selective excitation according to the present invention entails more complex pattern changes, such as changes in feature size and/or orientation, and the use of more complex patterns.

As will be explained with reference to FIGS. 7A-7B, in one embodiment the selective excitation patterns 602, 604, 606 are generated by a synthetic aperture optics apparatus for structured illumination (also referred to as patterned excitation or standing wave excitation). The selective excitation patterns 602, 604, 606 are generated optimized to the microparticle array 502. For example, as will be explained with reference to FIG. 10, the selective excitation patterns 602, 604, 606 determine the distribution of samples in the frequency domain. The extent of the distribution of samples in the frequency domain is matched to the feature size 608 of the microparticle array. The selective excitation of the nucleic acid microparticles 204 is performed at a resolution sufficient to resolve the individual microparticles. For example, a sine wave illumination with a period that is twice the spacing between the microparticle centers 204 may be used to generate the selective excitation patterns 602, 604, 606, although a variety of other illumination periods can be used in other examples.

Also, the sequence and number of the excitation patterns are designed to ensure that relatively low-resolution images of the excited microparticle array 502 still produce an efficient yet complete and accurate representation of the optical signatures of the microparticles 204, and correspondingly the sequence information in the microparticle array 502. For example, as will be explained with reference to FIG. 10, the selective excitation patterns 602, 604, 606 determine the distribution of samples in the frequency domain. The number of samples in the frequency domain is matched to the feature density of the optical signatures of the microparticle array 502.

Referring back to FIG. 5, after the last excite-and-image cycle is complete at the last excitation pattern 510, it is determined 514 whether the current FOV is the last FOV for the microparticle array 502. If the current FOV is not the last FOV, the microparticle array 502 is translated (move stage) 516 to the next FOV and the excite-and-image cycles in steps 506, 508, 510, 512 are repeated for that next FOV. For example, the microparticle array 502 can be moved 516 to expose another FOV of the microparticle array 502. Alternatively, the structured illumination apparatus that generated the selective excitation patterns can be moved to expose another FOV of the microparticle array 502.

After the entire microparticle array 502 has been imaged (i.e., after the last FOV in step 514), it is determined 518 whether the microparticle array should undergo another cycle of sequencing reactions. If the current reaction 504 is not the last reaction, a new cycle of sequencing reactions 504 is performed with same or different sequencing reagents, and then steps 506 through 518 are repeated. After the final sequencing-reaction cycle 518, image processing 520 is performed on the optical signature data of the microparticle array 502 to extract the sequence data 522 contained in the DNA molecules in the microparticle array 502.

Figure 7A:
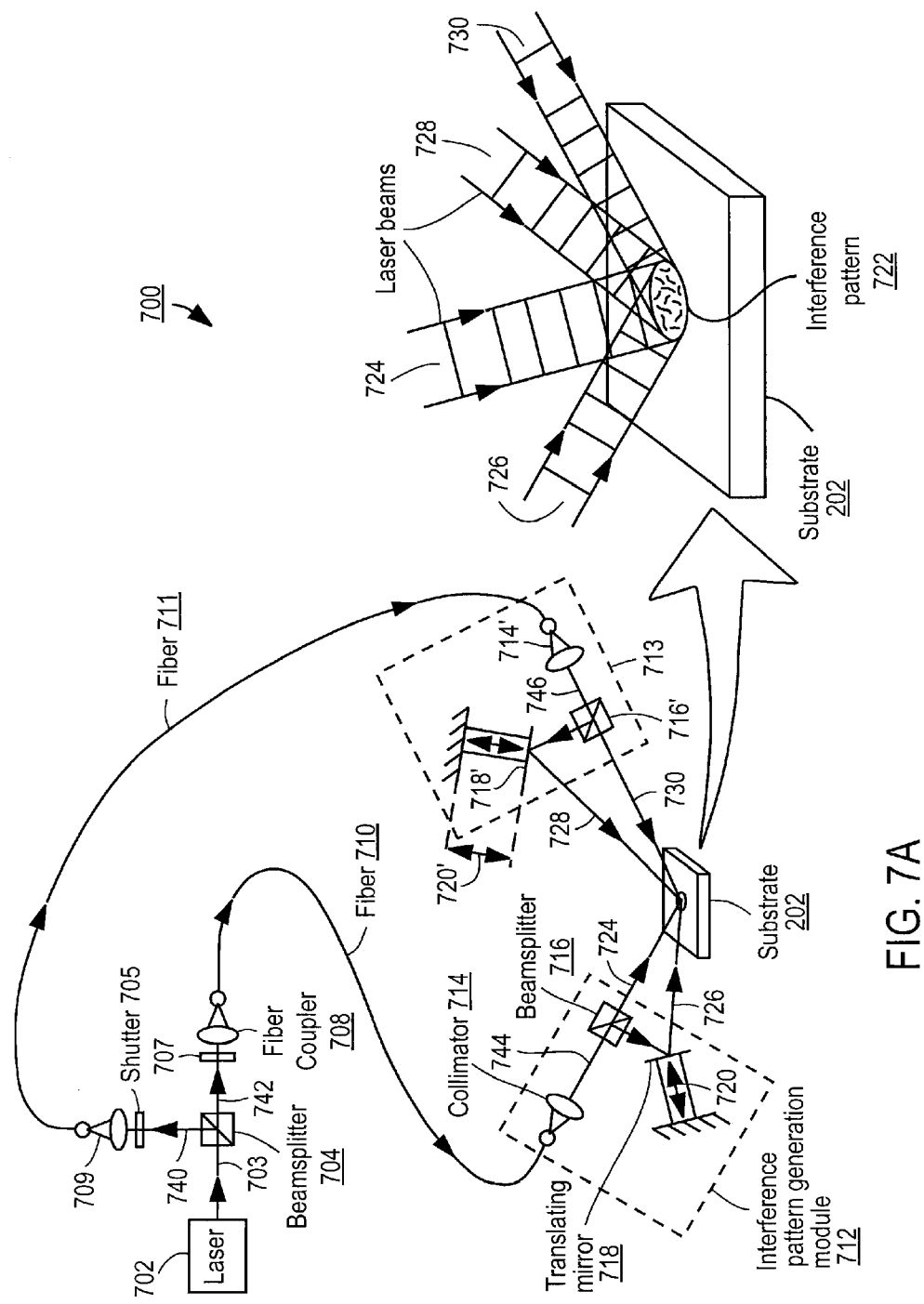
FIG. 7A illustrates a structured illumination apparatus for selectively exciting the microparticles, according to one embodiment of the present invention.

FIG. 7A illustrates a synthetic aperture optics structured illumination apparatus for selectively exciting the microparticles, according to one embodiment of the present invention. At a high level, the structured illumination apparatus generates multiple mutually-coherent laser beams, the interference of which produces interference patterns. Such interference patterns are projected onto the microparticle array 502 and selectively excite the microparticles 204. Using the interference of multiple laser beams to generate the interference patterns is advantageous for many reasons. For example, this enables high-resolution excitation patterns with extremely large FOV and DOF. Although the structured illumination apparatus of FIG. 7A (and FIG. 7B) is described herein with the example of generating excitation patterns for the microparticle array 502, it should be noted that the structured illumination apparatus of FIG. 7A (and FIG. 7B) can be used for any other type of application to generate excitation patterns for any other type of target.

Referring to FIG. 7A, the structured illumination apparatus 700 includes a laser 702, a beam splitter 704, shutters 705, 707, fiber couplers 708, 709, a pair of optical fibers 710, 711, and a pair of interference pattern generation modules 712, 713. The beam 703 of the laser 702 is split by the beam splitter 704 into two beams 740, 742. A pair of high-speed shutters 705, 707 is used to switch each beam 740, 742 "on" or "off" respectively, or to modulate the amplitude of each beam 740, 742, respectively. Such switched laser beams are coupled into a pair of polarization-maintaining optical fibers 711, 710 via fiber couplers 709, 708. Each fiber 711, 710 is connected to a corresponding interference pattern generation module 713, 712, respectively. The interference pattern generation module 713 includes a collimating lens 714', a beam splitter 716', and a translating mirror 718', and likewise the interference pattern generation module 712 includes a collimating lens 714, a beam splitter 716, and a translating mirror 718.

The beam 744 from the optical fiber 710 is collimated by the collimating lens 714 and split into two beams 724, 726 by the beam splitter 716. The mirror 718 is translated by an actuator 720 to vary the optical path-length of the beam 726. Thus, an interference pattern 722 is generated on the substrate 202 in the region of overlap between the two laser beams 724, 726, with the pattern changed by varying the optical path-length of one of the beams 726 (i.e., by modulating the optical phase of the beam 726 by use of the translating mirror 718).

Similarly, the beam 746 from the optical fiber 711 is collimated by the collimating lens 714' and split into two beams 728, 730 by the beam splitter 716'. The mirror 718' is translated by an actuator 720' to vary the optical path-length of the beam 728. Thus, the interference pattern 722 is generated on the substrate 202 in the region of overlap between the two laser beams 728, 730, with the pattern changed by varying the optical path-length of one of the beams 728 (i.e., by modulating the optical phase of the beam 728 by use of the translating mirror 718'). In fact, the interference pattern 722 is generated on the substrate 202 in the region of overlap between the four laser beams 726, 724, 728, 730. In one embodiment, for generating sinusoidal interference patterns, only two phases (0 and 90 degrees) or three phases (0, 120, and 240 degrees) are used and are sufficient for selective excitation of microparticles.

While this implementation illustrated in FIG. 7A is used for its simplicity, various other approaches can be used within the scope of the present invention. For example, the amplitude, polarization, direction, and wavelength, in addition to or instead of the optical amplitude and phase, of one or more of the beams 724, 726, 728, 730 can be modulated to change the excitation pattern 722. Also, the structured illumination can be simply translated with respect to the microparticle array to change the excitation pattern. Similarly, the microparticle array can be translated with respect to the structured illumination to change the excitation pattern. Also, various types of optical modulators can be used in addition to or instead of the translating mirrors 718, 718', such as acousto-optic modulators, electro-optic modulators, and micro-electro-mechanical systems (MEMS) modulators. In addition, although the structured illumination apparatus of FIG. 7A (and FIG. 7B) is described herein as using a laser 702 as the illumination source for coherent electromagnetic radiation, other types of coherent electromagnetic radiation sources such as an SLD (super-luminescent diode) may be used in place of the laser 702.

Also, although FIG. 7A illustrates use of four beams 724, 726, 728, 730 to generate the interference pattern 722, larger number of laser beams can be used by splitting the source laser beam into more than two beams. For example, 64 beams may be used to generate the interference pattern 722. In addition, the beam combinations do not need to be restricted to pair-wise combinations. For example, three beams 724, 726, 728, or three beams 724, 726, 730, or three beams 724, 728, 730, or three beams 726, 729, 730, or all four beams 724, 726, 728, 730 can be used to generate the interference pattern 722. Typically, a minimal set of beam combinations is chosen as necessary to maximize speed. In one embodiment, the number of beam combinations is matched to the amount of unknown information in the microparticle array 502. For example, once the locations of the microparticles in the microparticle array 502 are known, the optical signatures of the microparticles, and subsequently the sequence information, can be determined using a relatively small number of excitation patterns. Also, the beams can be collimated, converging, or diverging. Although different from the specific implementations of FIGS. 7A and 7B and for different applications, additional general background information on generating interference patterns using multiple beam pairs can be found in (i) U.S. Pat. No. 6,016,196, issued on Jan. 18, 2000 to Mermelstein, entitled "Multiple Beam Pair Optical Imaging," (ii) U.S. Pat. No. 6,140,660, issued on Oct. 31, 2000 to Mermelstein, entitled "Optical Synthetic Aperture Array," and (iii) U.S. Pat. No. 6,548,820, issued on Apr. 15, 2003 to Mermelstein, entitled "Optical Synthetic Aperture Array," all of which are incorporated by reference herein.

Figure 7B:
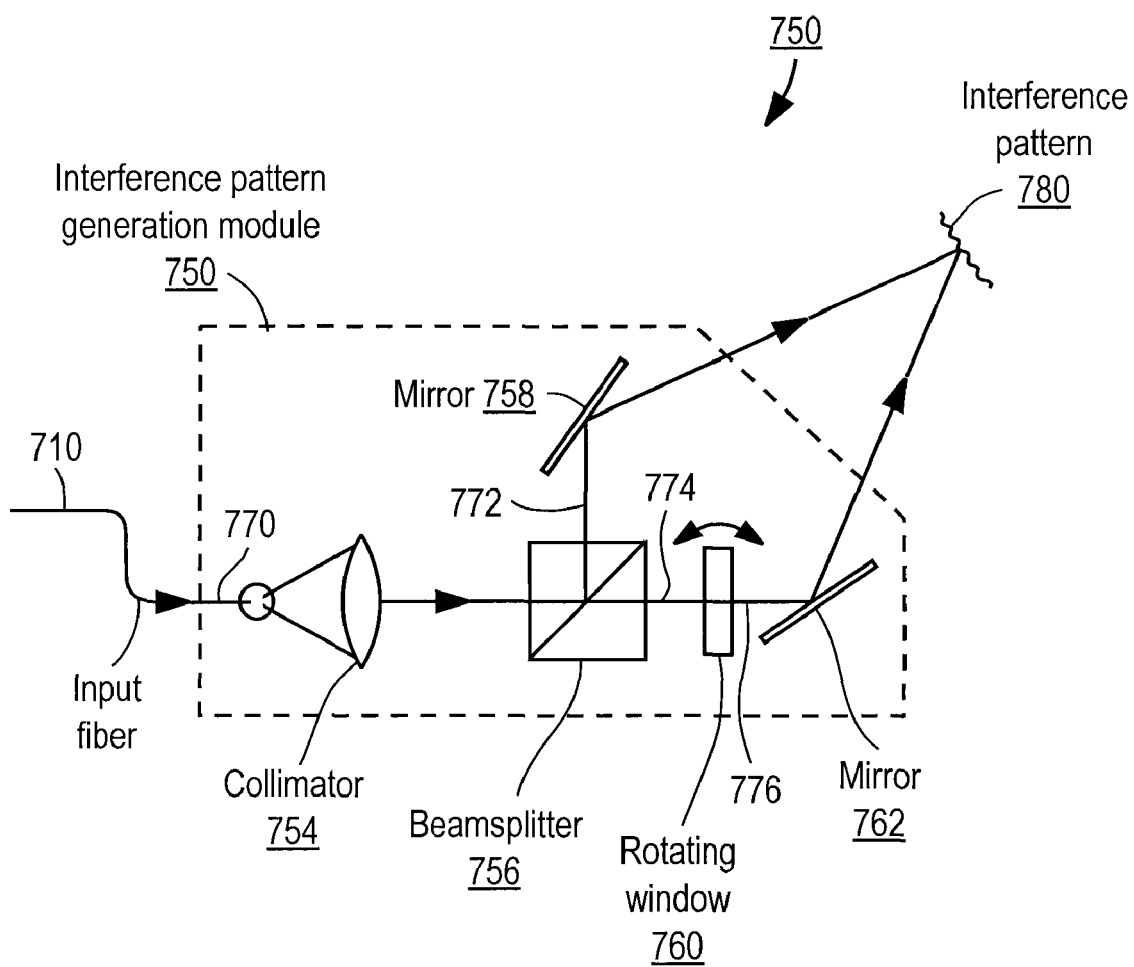
FIG. 7B illustrates a different type of interference pattern generation module that can be used with the structured illumination apparatus of FIG. 7A, according to another embodiment of the present invention.

FIG. 7B illustrates a different type of interference pattern generation module that can be used with the apparatus of FIG. 7A, according to another embodiment of the present invention. The interference pattern generation module 750 of FIG. 7B can be used in place of the interference pattern generation module 712 or 713 of FIG. 7A. Although FIG. 7B illustrates the situation where the interference pattern generation module 712 of FIG. 7A is replaced by the interference pattern generation module of 750 of FIG. 7B, the interference pattern generation module 713 can be similarly replaced by the interference pattern generation module of 750 of FIG. 7B.

Referring to FIG. 7B, the output beam 770 of the fiber 710 is collimated by the collimator 754 and split by the beam splitter 756 into two beams 772, 774. An optical window 760 is inserted into the optical path of one beam 774 and rotated, using a galvanometer, to modulate the optical path-length of the beam 774, thereby modulating the optical phase of the corresponding beam 774 and generate a modulated beam 776. Having only one phase modulator (rotating optical window 760) for every two beams makes the design of the interference pattern generation module 750 compact and efficient. Two stationary mirrors 758, 762 reflect the beams 772, 776, respectively, to generate an interference pattern 780 while maintaining approximately matching optical path-lengths.

The structured illumination apparatus of FIGS. 7A and 7B have a number of technical advantages compared to conventional structured illumination apparatuses. These advantages include that:

(i) The use of the interference of multiple lasers beams to generate high-resolution excitation patterns enables an extremely large FOV and DOF that is not achievable using a conventional lens projection system.

(ii) The optical fibers 710, 711 used to deliver the laser beams eliminate the transmission of vibration from the laser 702 source, which provides better pointing stability and better manufacturability.

(iii) The modularized design using interference pattern generation modules provide more flexible beam geometry design, which enables large numbers of beams to be used by reducing complexity and cost of manufacturing.

(iv) The optical fiber-based design enables a compact and lightweight apparatus that provides better mechanical and thermal stability. The compact assembly also minimizes free-space beam propagation, reducing disturbances caused by atmospheric turbulence.

(v) The interference pattern generation module of FIG. 7B provides nominally matched optical path-lengths, which eliminates the need for a single longitudinal mode laser source.

(vi) The optical fiber-based design performs the beam-splitting into two stages (one stage at beam splitter 704 and another stage at the beam splitters 716, 716' in the interference module generation modules 712, 713), such that temperature variations and mechanical disturbances of the fibers do not affect the interference pattern significantly.

(vii) Because only two phases (0 and 90 degrees) or three phases (0, 120, and 240 degrees) are used for generating sinusoidal interference patterns, as opposed to 8 or more phases, the time required for data acquisition is greatly reduced.

(viii) The use of shutters and rotating optical windows for amplitude and phase modulation enables a compact and lightweight apparatus with low cost, simple control electronics, and high optical efficiency. For example, the optical efficiency of the interference pattern generation module 750 shown in FIG. 7B can be greater than 95%.

Figure 7C:
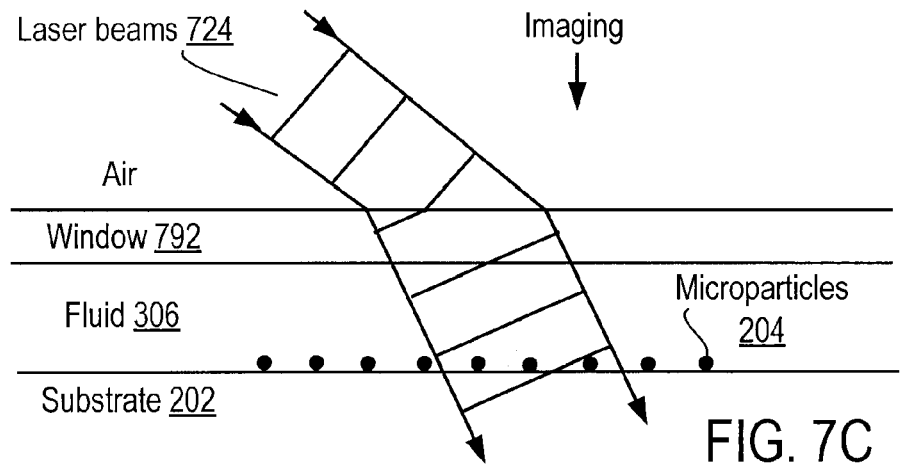
FIGS. 7C, 7D, and 7E illustrate how the beams from the structured illumination apparatus of FIG. 7A or FIG. 7B can be coupled into fluid to illuminate the microparticles, according to embodiments of the present invention.
Figure 7D:
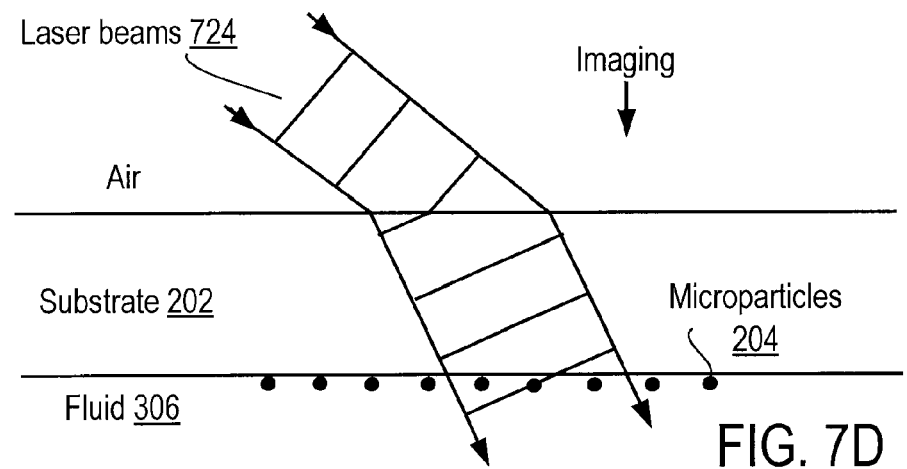
Figure 7E:
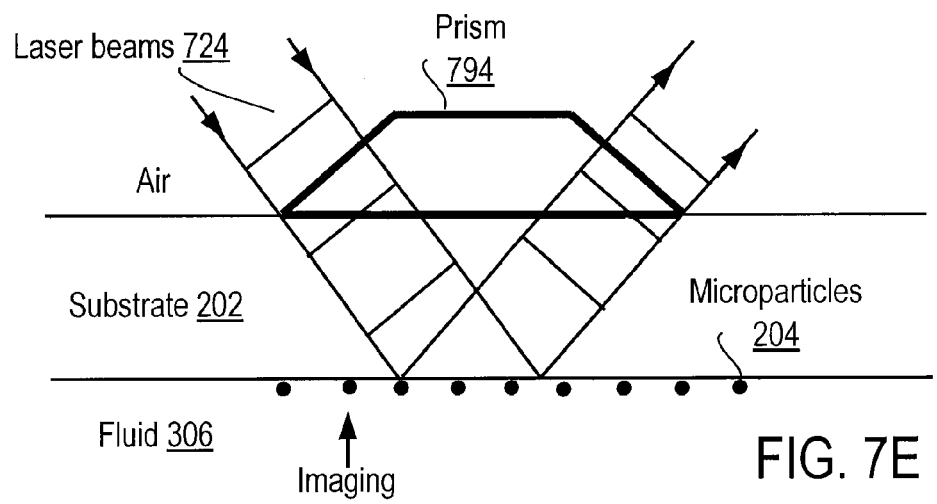

FIGS. 7C, 7D, and 7E illustrate how the beams from the structured illumination apparatus of FIG. 7A or FIG. 7B can be coupled into fluid to illuminate the microparticles, according to embodiments of the present invention. Specifically, FIG. 7C illustrates the laser beams 724 entering the fluid 306 through a window 792 to illuminate and selectively excite the microparticles 204 on the substrate 202 of an upright microparticle array 502. The microparticles 204 can be imaged through the window 792. FIG. 7D illustrates the laser beams 724 entering the fluid 306 through the back side of the substrate 202 (i.e., the side of the substrate 202 opposite to the side where the microparticles 204 are placed) to illuminate an inverted microparticle array 502. The microparticles 204 can be imaged through the substrate 202. FIG. 7E illustrates the laser beams 724 entering the fluid 306 through a coupling prism 794 to illuminate and selectively excite the microparticles 204 on the substrate 202 of an inverted microparticle array 502 in a TIR (total internal reflection) illumination configuration off of the substrate 202. The microparticles 204 can be imaged through the substrate 202. For clarity, only one beam is illustrated in FIGS. 7C-7E.

Figure 8:
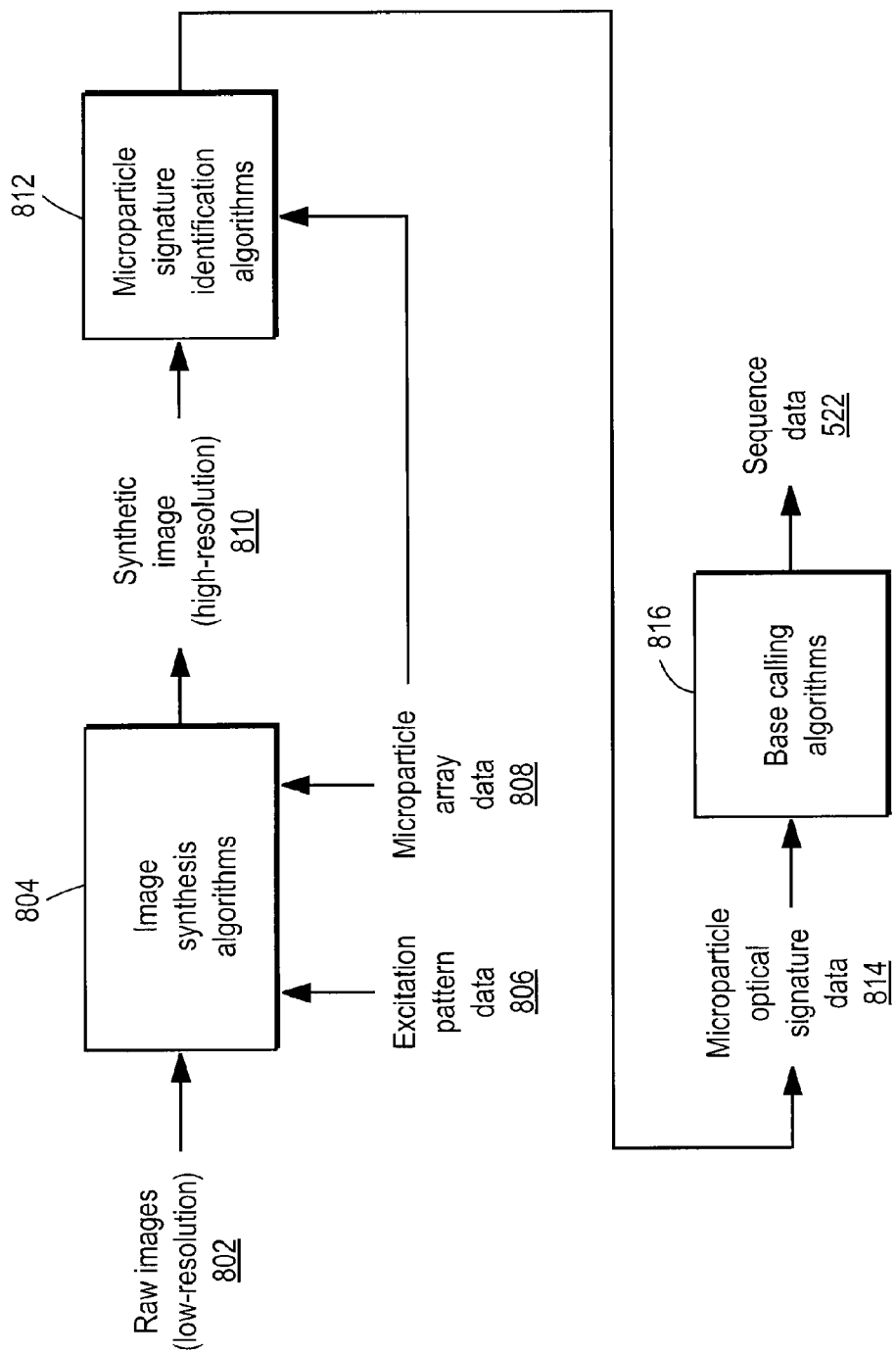
FIG. 8 illustrates the image processing step of FIG. 5 for DNA sequencing in more detail, according to one embodiment of the present invention.

FIG. 8 illustrates the image processing 520 of FIG. 5 for sequencing in more detail, according to one embodiment of the present invention. The raw images 802 of the selectively-excited microparticles output from the optical imaging 508 (FIG. 5) are input into image synthesis algorithms 804. Note that the raw images 802 are low-resolution images—the selective excitation 506 (FIG. 5) and the knowledge of the selective excitation patterns eliminate the need for high-resolution images. The low resolution of the raw images is insufficient to resolve the individual microparticles. However, the image synthesis algorithms 804 process the raw images 802, together with information 806 about the excitation patterns used to excite the microparticles and information 808 about the microparticle array 502 (such as the sizes and locations of the microparticles), to generate a synthetic high-resolution image 810 of the microparticle array 502. The synthetic image 810 is input into microparticle signature identification (MSI) algorithms 812 that process the synthetic image 810 together with the information 808 about the microparticle array 502 to determine the optical signature 814 of each microparticle. The microparticle optical signature data 814 is input into base-calling algorithms 816 that produce a sequence 522 of DNA bases. While the implementation of FIG. 8 is advantageous due to its transparency and simplicity, various other approaches can be used for the image processing 520.

Figure 9:
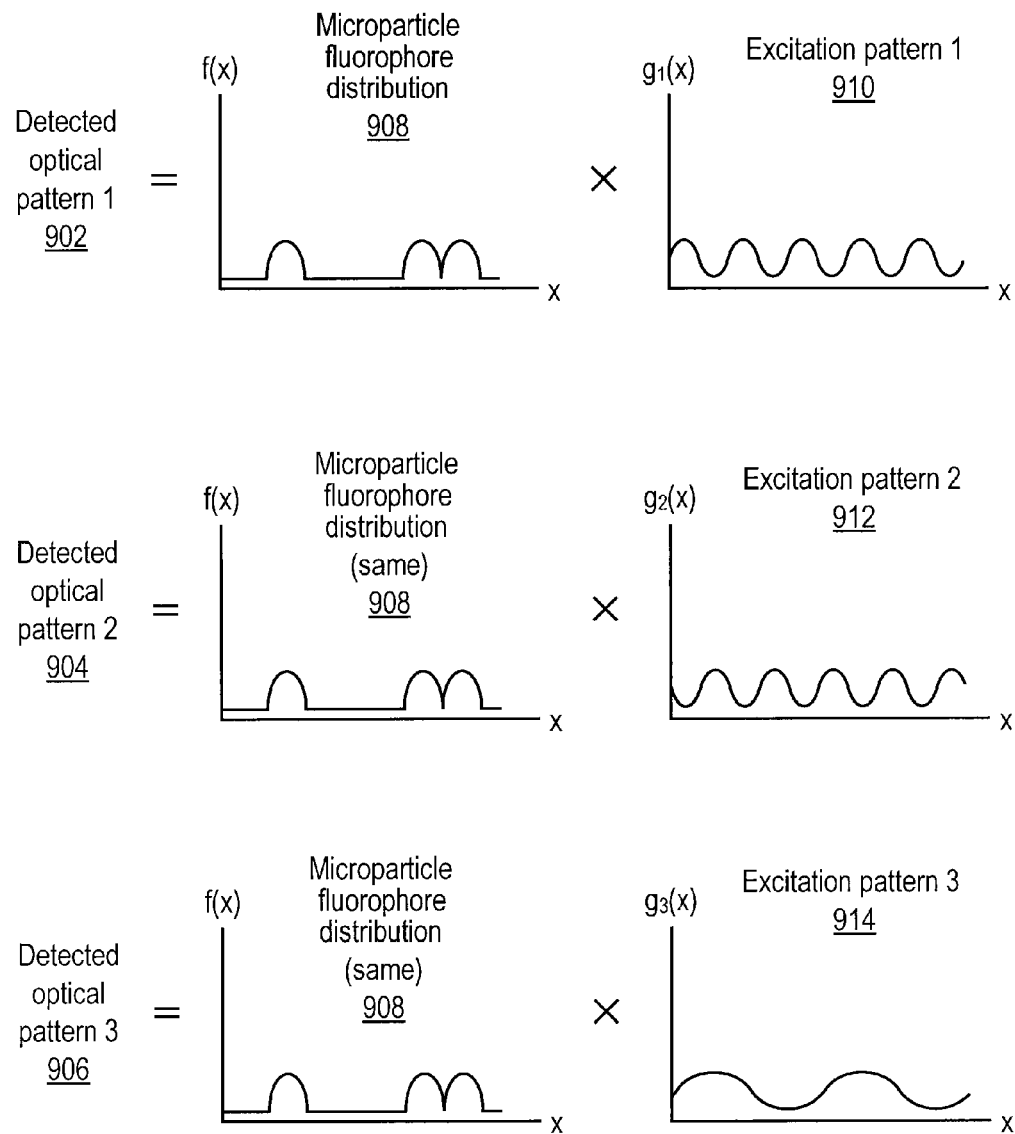
FIG. 9 illustrates how the detected optical pattern can be modeled as a product of the microparticle fluorophore distribution function and the excitation pattern, according to one embodiment of the present invention.

The image synthesis algorithms 804 in FIG. 8 take advantage of the property that the interference pattern generation modules 712, 713 (FIG. 7) generate excitation patterns that are well-approximated as sinusoids or sums of sinusoids. FIG. 9 illustrates how the detected optical pattern can be modeled as a product of the microparticle fluorophore distribution function and the excitation pattern. As shown one-dimensionally in FIG. 9, the optical patterns 802 (FIG. 8) detected by the optical imaging 508 (FIG. 5) can then be expressed as the product of a microparticle fluorophore distribution function and a sinusoidal function (or sums of sinusoidal functions), which lends itself to a Fourier sum representation. For example, the detected optical pattern 902 can be a product of the microparticle fluorophore distribution function (f(x)) 908 and the excitation pattern ($g_1(x)$) 910. The detected optical pattern 904 can be a product of the same microparticle fluorophore distribution function (f(x)) 908 and a different excitation pattern ($g_2(x)$) 912 (which in this example is 180 degrees out of phase with the excitation pattern ($g_1(x)$) 910). The detected optical pattern 906 can be a product of the same microparticle fluorophore distribution function (f(x)) 908 and another different excitation pattern ($g_3(x)$) 914 (which in this example has a different period compared to the excitation patterns 910, 912).

Once the raw image data 802 is expressed as a Fourier sum, the problem of generating a synthetic high-resolution image 810 can be cast as a general Fourier-inversion problem, which can be solved using a great variety of well-known methods. Note that a more general implementation of the image synthesis algorithms does not assume that the excitation patterns are sinusoids or sums of sinusoids. In this case, the raw image 802 data can be expressed as a more general matrix multiplication. The problem of generating a synthetic high-resolution image 810 can then be cast as a general matrix-inversion problem, which can be solved using a great variety of well-known methods.

Figure 10:
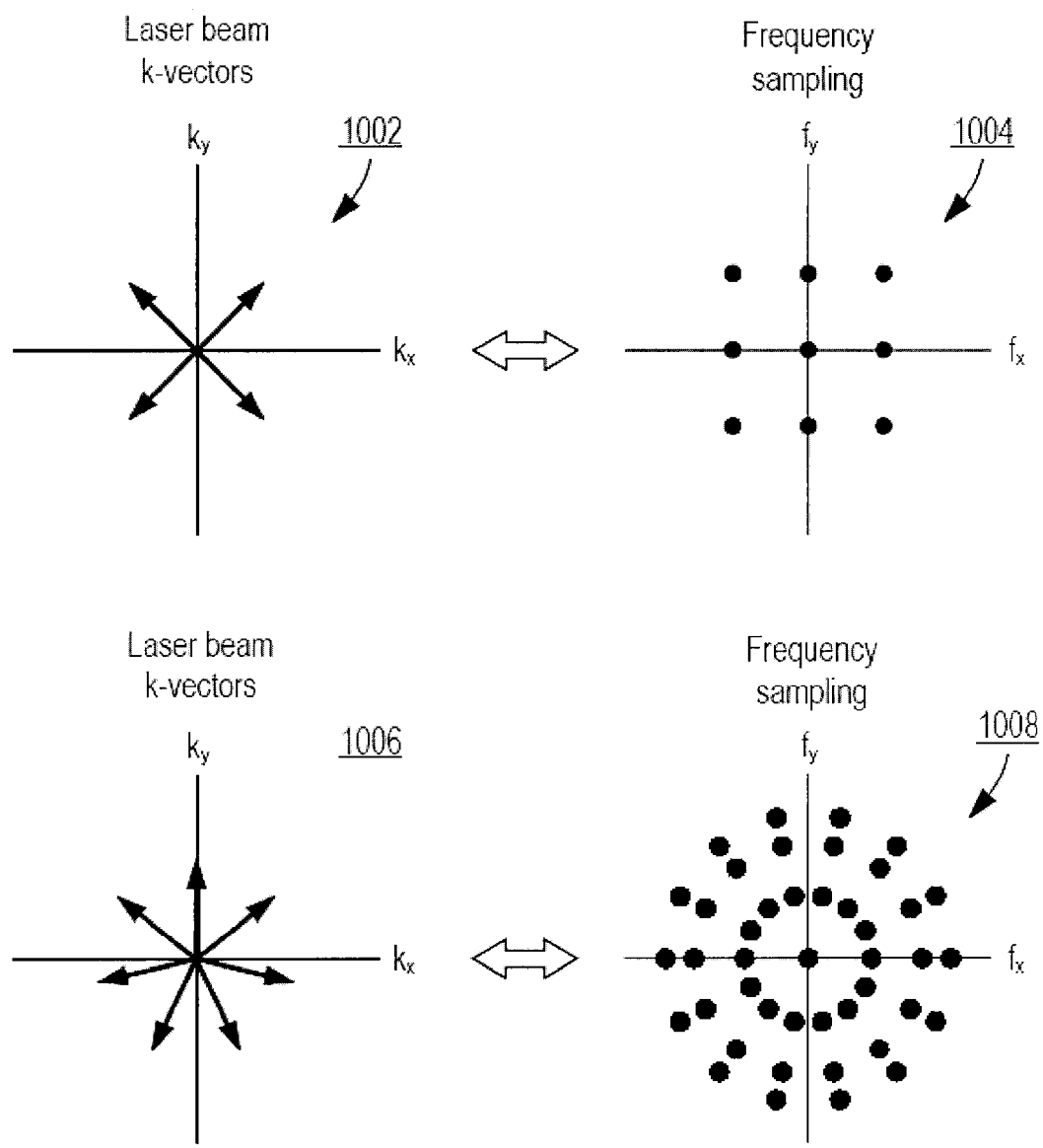
FIG. 10 illustrates the relationship between the sampling pattern in the frequency domain and the geometry of laser beams used to generate the excitation patterns, according to one embodiment of the present invention.

FIG. 10 illustrates the relationship between the sampling pattern in the frequency domain and the geometry of laser beams used to generate the excitation patterns. As shown in FIG. 10, the distribution of such samples in the frequency domain is determined by the geometry of the laser beams in the structured illumination apparatus. For example, if the laser beams have k-vectors in the geometry 1002, the frequency samples would have a rectilinear distribution 1004 (also referred to as a 2DFT distribution, a Cartesian distribution, or a uniform distribution). For another example, if the laser beams have k-vectors in the geometry 1006, the frequency samples would have a non-rectilinear distribution 1008.

Figure 11:
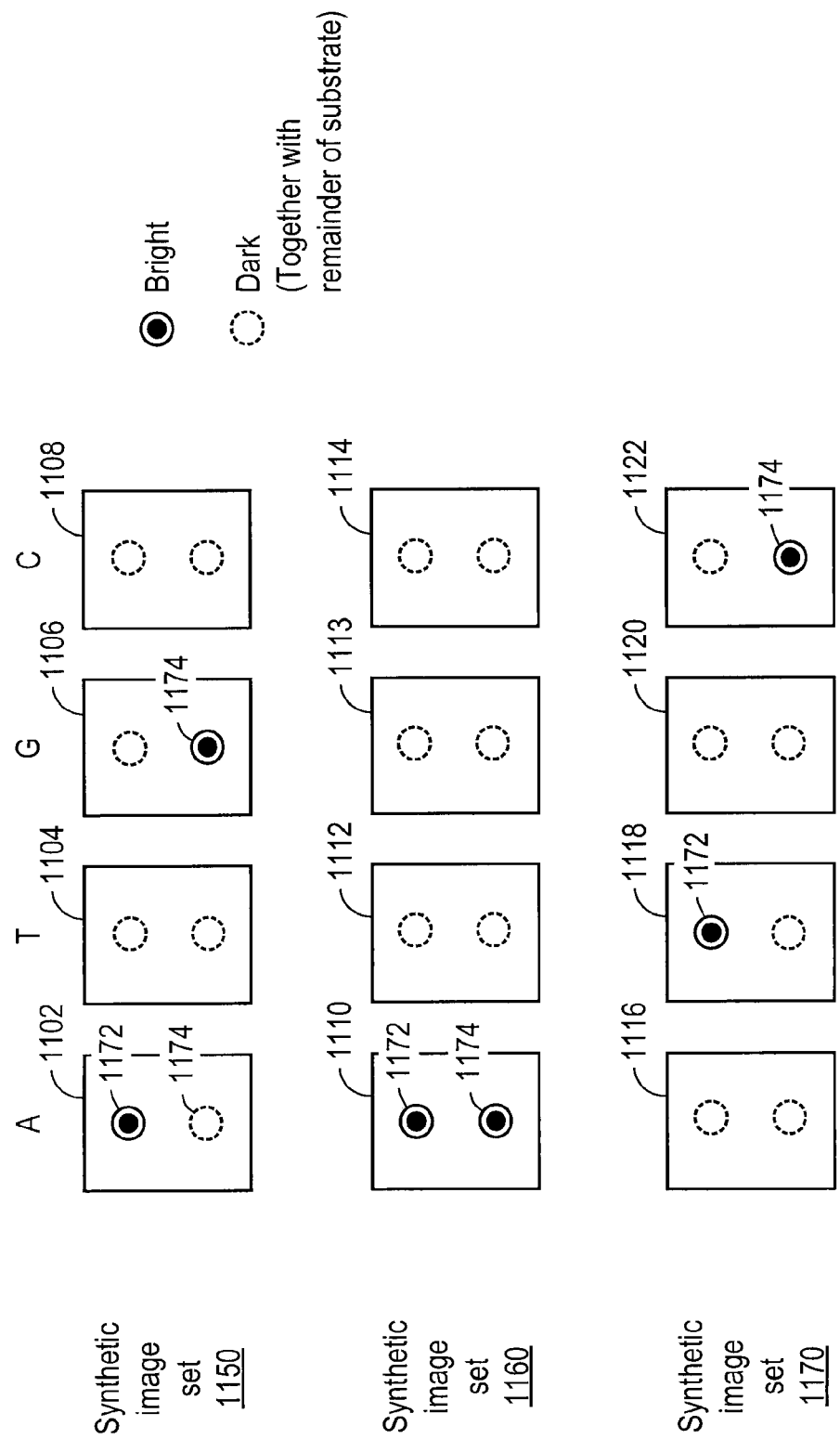
FIG. 11 conceptually illustrates the process of identifying the DNA base pairs for each microparticle, according to one embodiment of the present invention.

The MSI algorithms 812 and base-calling algorithms 816 in FIG. 8 take as input the high-resolution synthetic images 810 of the microparticle array and produce a sequence 522 of DNA bases for each microparticle. FIG. 11 conceptually illustrates this process of identifying the DNA bases for each microparticle, according to one embodiment of the present invention. Referring to FIG. 11, each of the 12 images 1102 through 1122 shows the same FOV, and there are two sequencing microparticles 1172, 1174 in each FOV in this example.

The synthetic image set 1150 illustrates the microparticles 1172, 1174 after a first sequencing reaction cycle. During that first reaction cycle, the microparticles 1172, 1174 take on one of four optical signatures corresponding to a first unknown DNA base for each microparticle 1172, 1174. The synthetic image set 1150 is comprised of four high-resolution synthetic images 810, each of which is optimized to detect one of the four optical signatures. The first image 1102 of the set 1150 is optimized to detect the optical signature corresponding to the DNA base "a." The second image 1104 of the set 1150 is optimized to detect the optical signature corresponding to the DNA base "t." The third image 1106 of the set 1150 is optimized to detect the optical signature corresponding to the DNA base "g." The fourth image 1106 of the set 1150 is optimized to detect the optical signature corresponding to the DNA base "c."

The second synthetic image set 1160 illustrates the microparticles 1172, 1174 after a second sequencing reaction cycle. During that second reaction cycle, the microparticles 1172, 1174 take on one of four optical signatures corresponding to a second unknown DNA base for each microparticle 1172, 1174. The synthetic image set 1160 consists of four high-resolution synthetic images 810, each of which is optimized to detect one of the four optical signatures. The first image 1110 of the set 1160 is optimized to detect the optical signature corresponding to the DNA base "a." The second image 1112 of the set 1160 is optimized to detect the optical signature corresponding to the DNA base "t." The third image 1113 of the set 1160 is optimized to detect the optical signature corresponding to the DNA base "g." The fourth image 1114 of the set 1160 is optimized to detect the optical signature corresponding to the DNA base "c."

The third synthetic image set 1170 illustrates the microparticles 1172, 1174 after a third sequencing reaction cycle. During that third reaction cycle, the microparticles 1172, 1174 take on one of four optical signatures corresponding to a third unknown DNA base for each microparticle 1172, 1174. The synthetic image set 1170 consists of four high-resolution synthetic images 810, each of which is optimized to detect one of the four optical signatures. The first image 1116 of the set 1170 is optimized to detect the optical signature corresponding to the DNA base "a." The second image 1118 of the set 1170 is optimized to detect the optical signature corresponding to the DNA base "t." The third image 1120 of the set 1170 is optimized to detect the optical signature corresponding to the DNA base "g." The fourth image 1122 of the set 1170 is optimized to detect the optical signature corresponding to the DNA base "c."

In the synthetic image set 1150 corresponding to the first unknown DNA bases, the first microparticle 1172 is brightest in image 1102 corresponding to "a", and the second microparticle 1174 is brightest in the image 1106 corresponding to "g" but no microparticle is bright in the images 1104, 1108 corresponding to "t" and "c," respectively. In the synthetic image set 1160 corresponding to the second unknown DNA bases, both microparticles 1172, 1174 are brightest in the image 1110 corresponding to "a" but no microparticle is bright in the images 1112, 1113, 1114 corresponding to "t," "g" and "c," respectively. In the synthetic image set 1170 corresponding to the third unknown DNA bases, the first microparticle 1172 is brightest in the image 1118 corresponding to "t" and the second microparticle 1174 is brightest in the image 1122 corresponding to "c" but no microparticle is bright in the images 1116, 1120 corresponding to "a" and "g," respectively. Thus, in this simple conceptual example, the DNA sequence associated with the first microparticle 1172 is "aat" and the DNA sequence associated with the second microparticle 1174 is "gac." Although the example in FIG. 11 is illustrated above as using the brightness of the imaged microparticles to determine the sequence information, the sequence information can also be derived by detecting different spectral characteristics of the imaged microparticles.

In embodiments other than this simple conceptual example, the sequencing reaction cycles occur more or less frequently, and the number of optical signatures is more or less than four. For example, in one embodiment, sequencing reactions can occur between high-resolution synthetic images 1102, 1104 rather than between synthetic image sets 1150, 1160. In another embodiment, each microparticle 1172, 1174 takes on just one optical signature, and the absence of an optical signature conveys sequence information. In still another embodiment, each microparticle 1172, 1174 simultaneously takes on multiple optical signatures. In still another embodiment, the simple one-to-one correspondence between optical signatures and DNA bases is replaced by a more sophisticated scheme for encoding for DNA sequence information with optical signatures (e.g., two-base encoding). Note that there are a number of other conventional sequencing chemistries. The sequencing method of the present invention can be used and is compatible with the majority of sequencing chemistries.

Referring back to FIG. 8, the MSI algorithms 812 identify the microparticles 1172, 1174 in each high-resolution synthetic image 1102 through 1122, and extract the optical signature data for each microparticle. In practice, this can be accomplished by thresholding the image to identify the microparticles visible in each synthetic image, and then fitting the image of each microparticle with a two-dimensional Gaussian function to estimate location and brightness.

Referring back to FIG. 8, the base-calling algorithms 816 take as input the microparticle optical signature data 814 and generate a DNA sequence for each microparticle. The first step is to track the location of each microparticle through the sets of microparticle optical signature data 814. In practice, the position of the microparticle array is not identical in each imaging cycle. Consequently, the sets of microparticle optical signature data 814 typically require spatial registration. In one embodiment, spatial registration is aided by the use of registration microparticles mixed in with the sequencing microparticles. Typically, the registration microparticles are 1-micron diameter beads that are several times brighter than the sequencing microparticles. The brightness of the registration microparticles makes them easy to distinguish from the sequencing microparticles, and the ratio of registration microparticles to sequencing microparticles is low (approximately 1-to-1000) such that the sequencing throughput is not significantly affected. After the registration step, the second step is to determine the optical signature of each microparticle for each set of microparticle optical signature data 814. As stated above, each microparticle can take on one of four optical signatures in each set of microparticle optical signature data 814. The four optical signatures correspond to the four possible base calls (i.e., "a", "t", "g", and "c"). A quality metric is typically assigned to each base call. Note that a variety of conventional algorithms can be used to interpret the raw base calls, which are not the subject of the present invention and are not described herein.

Figure 12:
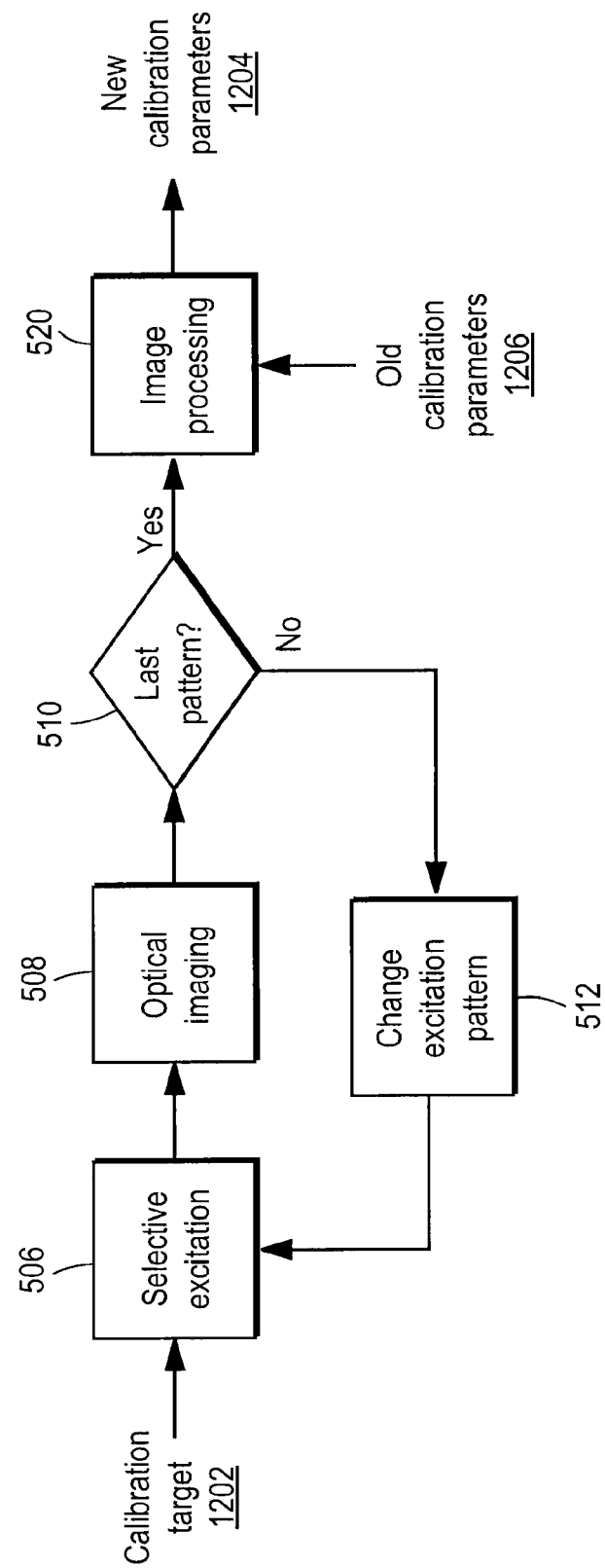
FIG. 12 illustrates a process for calibrating the structured illumination apparatus shown in FIG. 5, according to one embodiment of the present invention.

FIG. 12 illustrates a process for calibrating the structured illumination apparatus shown in FIG. 5. Calibration is done in order to know the excitation patterns with a certain degree of accuracy so that DNA sequence data can be successfully generated through image processing. For example, this excitation pattern data 806 (FIG. 8) is an input to the image synthesis algorithms 804 (FIG. 8). The typical calibration parameters in a synthetic aperture optics structured illumination apparatus as in FIGS. 7A and 7B are the direction, wavefront, shape, amplitude, polarization, wavelength, and relative optical phase of each beam 724, 726, 728, 730. Referring to FIG. 12, in one embodiment, calibration is performed by placing a calibration target 1202 in place of the microparticle array. A calibration target 1202 can in theory be any target with known features. For example, the calibration target 1202 can be a random array of fluorescent 1-micrometer diameter beads with substantially identical brightness. Similar to the process illustrated in FIG. 5, the calibration target 1202 is selectively excited 506 with an excitation pattern. The selectively-excited calibration target microparticle array is then imaged 508 using an optical microscope. The excitation pattern is then changed 512, and the excite-and-image cycle is repeated until the last pattern 510 is reached. After the last excite-and-image cycle is complete 510, the images are then processed 520. Based on knowledge of the calibration target 1202 and the old calibration parameters 1206 for the structured illumination apparatus, the content of the calibration images can be predicted. The discrepancy between the predicted calibration images (based on the old calibration parameters) and the measured calibration images through image processing 520 is used to generate new calibration parameters 1204.

Figure 13:
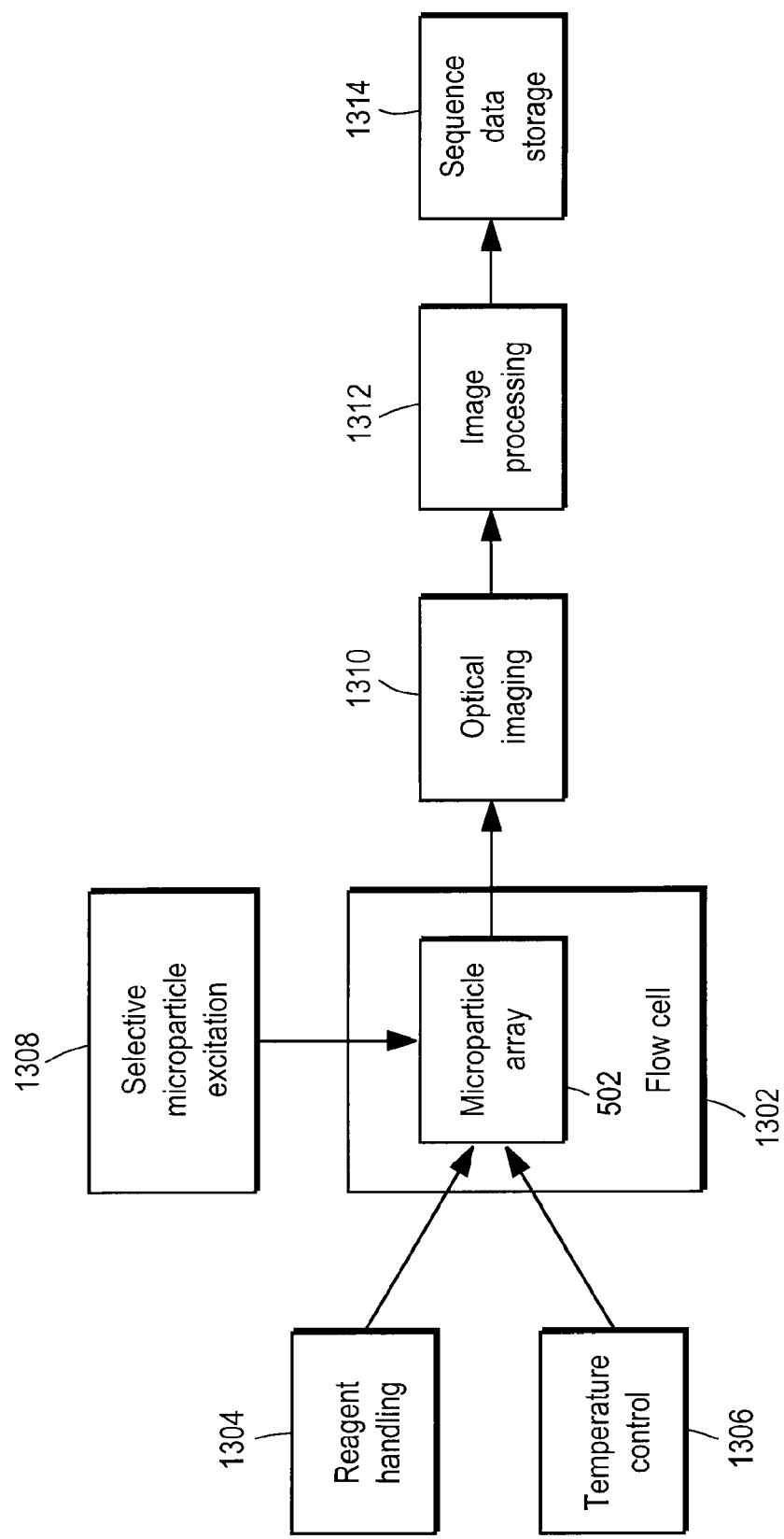
FIG. 13 conceptually illustrates the hardware system used for DNA sequencing by selective excitation of microparticles, according to one embodiment of the present invention.

FIG. 13 conceptually illustrates the hardware system used for sequencing by selective excitation of microparticles, according to one embodiment of the present invention. The hardware system includes a flow cell 1302, a reagent handling module 1304, a temperature control module 1306, a selective microparticle excitation module 1308, an optical imaging module 1310, an image processing module 1312, and a sequence data storage module 1314. The microparticle array 502 is typically located inside a flow cell 1302 that allows the microparticles to be exposed to sequencing reagents. The reagent handling module 1304 applies the reagents to expose the microparticle array 502 to the sequencing reagents. The temperature control module 1306 controls the reaction temperature of the flow cell 1302 at temperatures appropriate for reactions with the sequencing reagents. The selective microparticle excitation module 1308 selectively excites the microparticles as explained above, and the optical imaging module 1310 obtains images of the selectively-excited microparticles. The images of the selectively-excited microparticles are analyzed using image processing algorithms in the image processing module 1312 to extract the optical signatures of the microparticles and to generate the sequence information. The sequence information is stored in the sequence data storage module 1314.

Figure 14:
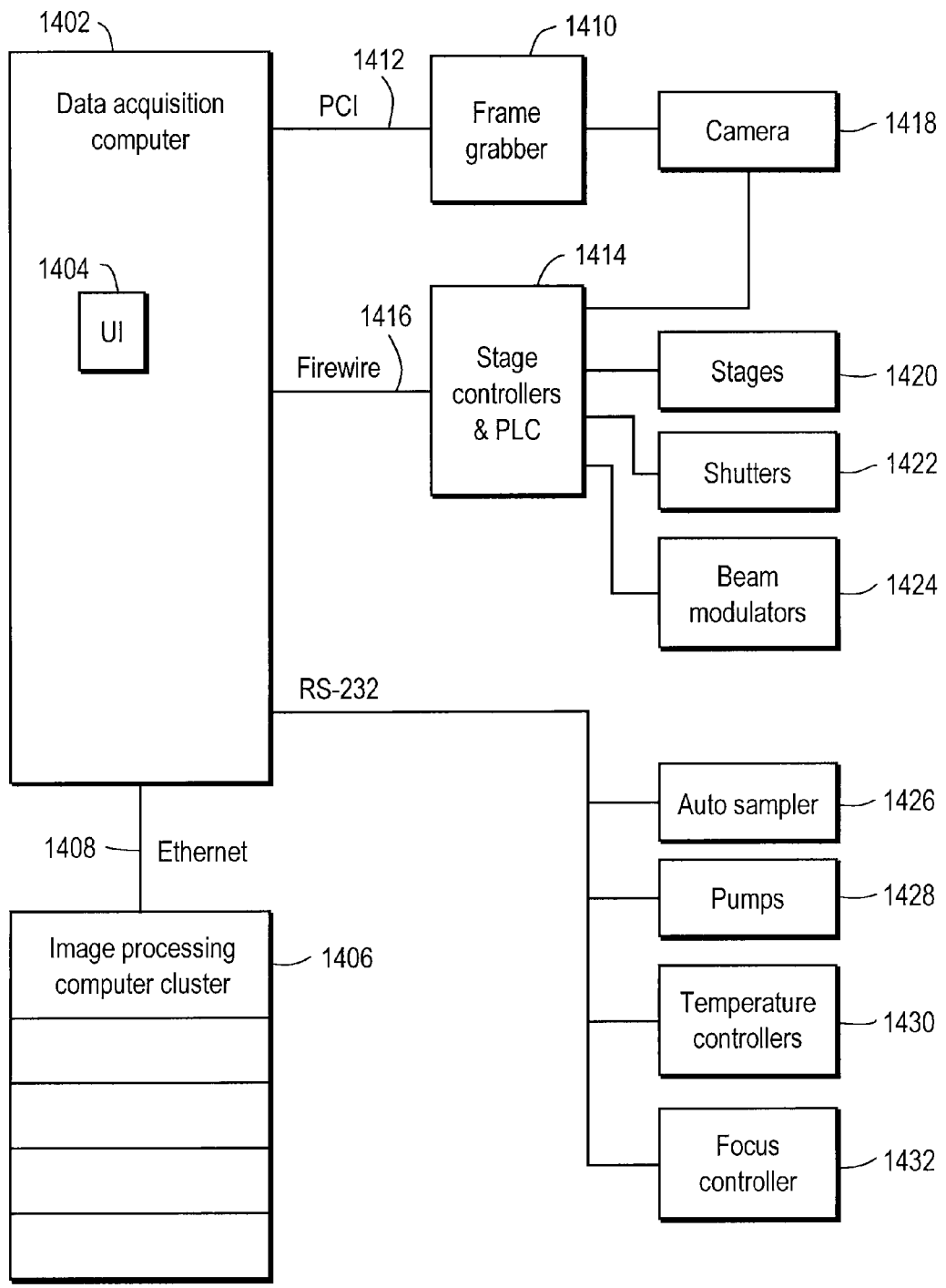
FIG. 14 illustrates the control system architecture for the sequencing hardware of FIG. 13, according to one embodiment of the present invention.

FIG. 14 illustrates the control system architecture for the sequencing hardware of FIG. 13. The control system architecture includes a data acquisition computer 1402 with a user interface 1404, a frame grabber 1410, a camera 1418, stage controllers with a programmable logic controller (PLC) 1414, (scanning) stages 1420, shutters 1422, beam modulators 1424, an autosampler 1426, pumps 1428, temperature controllers 1430, a focus controller 1432, and an image processing computer cluster 1406. The frame grabber 1410 is connected to the data acquisition computer 1402 through a peripheral component interconnect (PCI) interface 1412. The frame grabber 1410 and the camera 1418 together obtain images of the selectively-excited microparticles under control of the data acquisition computer 1402. For high speed, a PLC 1414 is used to control the shutters 1422 and beam modulators 1424 to change the excitation patterns, move the stages 1420, and trigger the camera 1418 to ensure tight synchronization. The PLC 1414 is connected to the data acquisition computer 1402 through a Firewire interface 1416. Other less-critically-timed hardware such as the autosampler 1426, pumps 1428, temperature controllers 1430, and the focus controller 1432 are controlled through a slower interface such as RS-232. The autosampler 1426 samples the sequencing reagents. The pumps 1428 pump the sequencing reagents into the flow cell 1302 to expose the microparticle array 502 to the sequencing reagents. The temperature controllers 1430 control the reaction temperature of the flow cell 1302 at temperatures appropriate for reactions with the sequencing reagents. The focus controller 1432 dynamically adjusts the focus of the optical imaging module 1310 to keep the microparticle array 502 in focus as the stages 1420 move. The data acquisition computer 1402 runs the user interface (UI) 1404, controls the variety of hardware, and receives image data from the camera 1418. The image data is sent over an Ethernet interface 1408 to a cluster of computers 1406 for image processing. The scanning stages 1420 and the focus controller 1432 enable large area microparticle arrays spanning multiple fields of view to be imaged.

Upon reading this disclosure, those of skill in the art will appreciate still additional alternative structural and functional designs for a method and system for nucleic acid sequencing through selective excitation of microparticles. For example, an excitation pattern can also be produced using a spatial light modulator (such as a liquid-crystal modulator or a MEMS-mirror-array modulator) and a projection lens. Thus, while particular embodiments and applications of the present invention have been illustrated and described, it is to be understood that the invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A method for sequencing nucleic acid microparticles, the method comprising the steps of:
    selectively exciting a calibration target by interference of a plurality of illumination beams;
    obtaining optical images of the excited calibration target;
    processing the optical images of the excited calibration target to generate a first optical image of the excited calibration target;
    predicting a second optical image of the excited calibration target based on first calibration parameters;
    generating second calibration parameters based on a difference between the first optical image and the second optical image;
    performing a sequencing reaction on the nucleic acid microparticles using one or more sequencing reagents, the nucleic acid particles being different from the calibration target;
    selectively exciting the nucleic acid microparticles in an excitation pattern using the second calibration parameters;
    obtaining optical images of the nucleic acid microparticles at a resolution insufficient to resolve individual microparticles; and
    processing the optical images of the nucleic acid microparticles using information on the excitation pattern to determine a presence or absence of at least one optical signature, the presence or absence of said at least one optical signature indicating sequence information of the nucleic acid microparticles.

2. The method of claim 1, wherein the nucleic acid microparticles are selectively excited at a resolution sufficient to resolve the individual microparticles.

3. The method of claim 1, wherein the excitation pattern is generated by interference of a plurality of illumination beams.

4. The method of claim 3, wherein the plurality of illumination beams undergo total internal reflection off a substrate on which the microparticles are placed.

5. The method of claim 3, wherein the excitation pattern generated by interference of the plurality of illumination beams produces sampling of a frequency domain in which an extent of the distribution of frequency samples is matched to a feature size of the microparticles.

6. The method of claim 3, wherein the excitation pattern generated by interference of the plurality of illumination beams produces a rectangle-like sampling of a frequency domain.

7. The method of claim 3, wherein the excitation pattern generated by interference of the plurality of illumination beams produces a non-rectilinear sampling of a frequency domain.

8. The method of claim 3, wherein selectively exciting the nucleic acid microparticles comprises:
    selectively exciting the nucleic acid microparticles in a first excitation pattern generated by interference of the illumination beams; and
    selectively exciting the nucleic acid microparticles in a second excitation pattern different from the first pattern generated by a different interference of the illumination beams.

9. The method of claim 8, wherein a phase of at least one of the illumination beams is modulated to generate the different interference of the illumination beams.

10. The method of claim 1, further comprising:
    performing another sequencing reaction on the nucleic acid microparticles;
    selectively exciting the nucleic acid microparticles in another excitation pattern;
    obtaining additional optical images of the nucleic acid microparticles at a resolution insufficient to resolve the individual microparticles; and
    processing the additional optical images of the nucleic acid microparticles using information on said another excitation pattern to determine a presence or absence of another optical signature, the presence or absence of said another optical signature indicating different sequence information of the nucleic acid microparticles.

11. The method of claim 1, wherein determining the presence or absence of at least an optical signature comprises determining that at least one of the microparticles exhibits an optical signature brighter or with a different spectral characteristic than other microparticles.

12. The method of claim 1, wherein processing the optical images of the nucleic acid microparticles comprises:
    generating a synthetic image of the microparticles with a higher resolution than the optical images based on the information on the excitation pattern;
    applying a microparticle signature identification algorithm to the synthetic image to generate microparticle optical signature data; and
    applying a base calling algorithm to determine the presence or absence of said at least one optical signature corresponding to the sequence information of the nucleic acid microparticles.

13. The method of claim 1, further comprising repeating the steps of selectively exciting the nucleic acid microparticles, obtaining optical images of the nucleic acid microparticles, and processing the optical images of the nucleic acid microparticles for a different field of view.

14. A method for sequencing nucleic acid microparticles, the method comprising the steps of:

performing a sequencing reaction on the nucleic acid microparticles using one or more sequencing reagents;

selectively exciting the nucleic acid microparticles with excitation patterns generated by interference of a plurality of illumination beams, at least one of the illumination beams being modulated in only two or three phases with respect to a period of an interference pattern to generate different sinusoidal interference patterns for use as the excitation patterns;

obtaining optical images of the nucleic acid microparticles at a resolution insufficient to resolve individual microparticles; and processing the optical images of the nucleic acid microparticles using information on the excitation patterns to determine a presence or absence of at least one optical signature, the presence or absence of said at least one optical signature indicating sequence information of the nucleic acid microparticles.

15. The method of claim 14, wherein the excitation patterns generated by interference of the plurality of illumination beams produces a rectangle-like sampling of a frequency domain.

16. The method of claim 14, wherein the excitation pattern generated by interference of the plurality of illumination beams produces a non-rectilinear sampling of a frequency domain.

* * * * *